US012364588B2

(12) United States Patent
Carpenter et al.

(10) Patent No.: US 12,364,588 B2
(45) Date of Patent: *Jul. 22, 2025

(54) EMBOLIC DEFLECTION DEVICE

(71) Applicant: Edwards Lifesciences AG, Nyon (CH)

(72) Inventors: Judith T. Carpenter, Moorestown, NJ (US); Jeffrey P. Carpenter, Moorestown, NJ (US); David A. Rezac, Lancaster, MA (US); Jeffrey C. Cerier, Franklin, MA (US); Richard C. Fortier, Concord, MA (US); Timothy W. Robinson, Sandown, NH (US)

(73) Assignee: Edwards Lifesciences AG, Nyon (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/643,899

(22) Filed: Apr. 23, 2024

(65) Prior Publication Data
US 2024/0268945 A1    Aug. 15, 2024

Related U.S. Application Data

(63) Continuation of application No. 17/664,822, filed on May 24, 2022, now Pat. No. 11,992,399, which is a (Continued)

(51) Int. Cl.
*A61F 2/01*    (2006.01)

(52) U.S. Cl.
CPC .............. *A61F 2/013* (2013.01); *A61F 2/011* (2020.05); *A61F 2002/016* (2013.01);
(Continued)

(58) Field of Classification Search
None
See application file for complete search history.

(56) References Cited

U.S. PATENT DOCUMENTS 6,245,088 B1 * 6/2001 Lowery ............ A61B 17/12109
606/200
6,458,153 B1    10/2002 Bailey et al.
(Continued)

FOREIGN PATENT DOCUMENTS

WO    2001049213 A2    7/2001
WO    2005102015 A2    11/2005

*Primary Examiner* — Katherine M Shi
*Assistant Examiner* — Lindsey Bachman
(74) *Attorney, Agent, or Firm* — Guy L. Cumberbatch; Joel B. German

(57) ABSTRACT

There is disclosed a porous emboli deflector for preventing cerebral emboli while maintaining cerebral blood flow during an endovascular or open surgical procedure. The device prevents the entrance of emboli of a size able to cause stroke (such as greater than 100 microns) from entering either the right or left common carotid arteries, and/or the right or left vertebral arteries by deflecting emboli downstream of these vessels. The device can be placed prior to any manipulation of the heart or aorta allowing maximal protection of the brain during the index procedure. The deflector has a low profile within the aorta which allows sheaths, catheters, or wires used in the index procedure to pass. Also disclosed are methods for insertion and removal of the deflector.

9 Claims, 35 Drawing Sheets

Related U.S. Application Data continuation of application No. 16/590,230, filed on Oct. 1, 2019, now abandoned, which is a continuation of application No. 15/153,552, filed on May 12, 2016, now Pat. No. 10,426,591, which is a continuation of application No. 12/685,591, filed on Jan. 11, 2010, now Pat. No. 9,339,367, which is a continuation-in-part of application No. PCT/US2010/020530, filed on Jan. 8, 2010, and a continuation-in-part of application No. 12/440,839, filed on Mar. 11, 2009, now Pat. No. 9,480,548, which is a continuation-in-part of application No. PCT/US2007/078170, filed on Sep. 11, 2007, which is a continuation-in-part of application No. 11/518,865, filed on Sep. 11, 2006, now Pat. No. 8,460,335.

(60) Provisional application No. 61/143,426, filed on Jan. 9, 2009.

(52) U.S. Cl.
CPC . *A61F 2002/018* (2013.01); *A61F 2230/0006* (2013.01); *A61F 2230/0008* (2013.01); *A61F 2230/0019* (2013.01); *A61F 2230/0021* (2013.01); *A61F 2230/005* (2013.01); *A61F 2230/008* (2013.01); *A61F 2230/0093* (2013.01); *A61F 2230/0095* (2013.01)

(56) References Cited

U.S. PATENT DOCUMENTS

| | | |
|---|---|---|
| 6,652,578 B2 | 11/2003 | Bailey et al. |
| 7,018,408 B2 | 3/2006 | Bailey et al. |
| 10,610,229 B2 * | 4/2020 | Jönsson ........... A61B 17/12159 |
| 2006/0025857 A1 | 2/2006 | Bergheim et al. |
| 2006/0161241 A1 * | 7/2006 | Barbut .................... A61F 2/013 |
| | | 623/1.15 |
| 2008/0125853 A1 | 5/2008 | Bailey et al. |

* cited by examiner

FIG. 15A FIG. 15B FIG. 15C FIG. 15D
FIG. 15E FIG. 15F FIG. 15G
FIG. 15H FIG. 15I FIG. 15J
FIG. 15K FIG. 15L

EMBOLIC DEFLECTION DEVICE

RELATED APPLICATIONS

This application is a continuation of U.S. patent application Ser. No. 17/664,822, filed May 24, 2022, which is a continuation of U.S. patent application Ser. No. 16/590,230, filed Oct. 1, 2019, which is a continuation of U.S. patent application Ser. No. 15/153,552, filed May 12, 2016, now issued as U.S. Pat. No. 10,426,591, which is a continuation of U.S. patent application Ser. No. 12/685,591, filed Jan. 11, 2010, now issued as U.S. Pat. No. 9,339,367, which claims priority under 35 U.S.C. § 119(e) as a nonprovisional of U.S. Provisional App. No. 61/143,426 filed on Jan. 9, 2009, and also claims priority under 35 U.S.C. § 120 as a continuation-in-part application of U.S. patent application Ser. No. 12/440,839 filed on Mar. 11, 2009, now issued as U.S. Pat. No. 9,480,548, which is a 35 U.S.C. § 371 national stage application of PCT Application No. PCT/US2007/078170 filed on Sep. 11, 2007, which is a continuation-in-part application of U.S. patent application Ser. No. 11/518,865, filed on Sep. 11, 2006, now issued as U.S. Pat. No. 8,460,335. Ser. No. 12/685,591 also claims priority as a continuation-in part application of PCT Application No. PCT/US2010/020530 filed on Jan. 8, 2010, which claims priority to the aforementioned U.S. Provisional App. No. 61/143,426 filed on Jan. 9, 2009. All of the aforementioned priority applications are hereby incorporated by reference in their entireties.

FIELD OF THE INVENTION

The invention generally relates to systems and method for deflection of embolic debris, such as during an operative, such as interventional or open surgical procedures in some embodiments.

BACKGROUND OF THE INVENTION

Endovascular procedures are being used more and more frequently to treat various cardiac and vascular surgical problems. Blocked arteries can be treated with angioplasty, endarterectomy, and/or stenting, using minimally invasive endovascular approaches. Aneurysms can be repaired by endovascular techniques. Another use for endovascular surgery is the treatment of cardiac valvular disease. Valvuloplasties are already being done endovascularly and percutaneous valve replacement is being tested in the United States and devices are already approved for use in Europe. One potential problem which is common to all these endovascular manipulations is that plaque found in the diseased vessels and valves can be dislodged and result in embolization. Similarly, a potential complication resulting from endovascular treatment of cardiac valves or the thoracic aorta is that the dislodged debris can embolize into the carotid vessels resulting in catastrophic consequences such as stroke or even death. Any procedure involving the passage of catheters across the aortic arch carries this risk of causing carotid emboli.

Patients requiring cardiac or aortic arch procedures are high risk candidates for having carotid disease. These procedures simultaneously place both carotid arteries at risk for emboli. The chance of causing a stroke by the placement of a protective device into both carotid arteries makes the risk of using these devices prohibitive. The time and skill necessary to selectively cannulate both carotid arteries for filter placement has also contributed to the decision not to use them despite the stroke risk of unprotected cardiac and aortic arch procedures.

Only a small number of devices have recently been developed which are designed to protect both carotid arteries at the same time. One device to date has come to market which protects both carotid arteries from emboli. Edwards Lifesciences' EMBOL-X™ is a device designed for use in open heart surgery during cardiopulmonary bypass. The device is a filtering screen inserted directly into the ascending aorta immediately beyond the heart, similar to a dryer vent screen. This screen filters all blood exiting the heart and bypass machine prior to allowing it to pass to the downstream circulation. Limitations of this device include its applicability only to open heart surgery, excluding its use in the vast array of endovascular procedures requiring protection. Adoption of the device has been hampered by ease of use, as operators often find it cumbersome. The device could not be adapted to endovascular procedures as the EMBOL-X™ completely spans the aorta. Thus, wires or catheters could not pass by it without breaking its protective seal. It has found limited adoption, and is chiefly employed for high risk patients undergoing open heart surgery. NeuroSonix Ltd. has developed the EmBlocker™, an ultrasound based scheme to deflect emboli away from the cerebral circulation during open cardiac procedures. An ultrasound probe is placed through the sternal wound and ultrasonic energy is directed at the blood flow in the aortic arch with the intent of deflecting emboli away from the cerebral circulation. Another proposed version for use in endovascular procedures is in the form of an externally applied "collar" around the neck of the patient, which would apply ultrasound through the neck with the hope of deflecting embolic particles away from the carotid circulation. It is known that the ultrasound beam can be tolerated only for brief periods of time and that it is turned off and on at different points during procedures. Thus, there would be a lack of complete protection from beginning to end of an open heart procedure or endovascular procedure.

One additional device being developed for aortic embolic protection is the SagaX AEPD™ which is placed in the aorta through a femoral artery and secured in position with wire bows pressing against the wall of the aorta and another vessel wall. A key difference and disadvantage of this device is that, when it is positioned to cover the vessels of the aortic arch, one of its bows spans the aorta. Although a catheter from the index procedure might be able to pass through the open loop of the bow there is the possibility for entanglement, of dislodging the device, or of pressing against the bow causing damage to the aortic wall. Another difference and disadvantage of this device includes its delivery through the as yet unprotected aorta. The device is delivered across the aortic arch, which could cause emboli, and is manipulated into position in the arch with deployment of its bows against vessel walls while the aorta is unprotected. Other differences and disadvantages include possible difficulty in positioning, difficulty in sealing it in position, and possible trauma to the vessel walls from the pressure of the bows.

Intravascular filtering devices of the prior art generally share certain additional disadvantages. For example, captured emboli reduce perfusion through the filter. In addition, closing the filter to withdraw the emboli from the body can be difficult depending upon the volume of entrapped emboli.

Thus, notwithstanding the efforts in the prior art, there remains a need for an embolic protection device of the type that can permit transluminal or surgical procedures in the vicinity of the heart, while protecting the cerebral vasculature.

SUMMARY OF THE INVENTION

Disclosed herein are systems and methods for embolic deflection, including systems for deployment and removal. In one embodiment, disclosed is a method of deflecting emboli flowing within a main vessel from entering a side branch vessel. The method includes the steps of advancing an emboli deflection device through a first side branch vessel and into the main vessel, and manipulating the deflection device such that it covers the opening to a second side branch vessel, wherein the deflection device permits blood flow from the main vessel into the second side branch vessel, but deflects emboli from entering the second side branch vessel without obstructing the lumen of the main vessel. The first side branch vessel could be, for example the brachiocephalic artery. The second side branch vessel could be, for example, the left common carotid artery. The main vessel could be the aorta. In some embodiments, the emboli deflection device can be advanced through a sheath that removably houses the emboli deflection device. The sheath could be, for example, no larger than 6 French in diameter.

In another embodiment, disclosed is a method of deflecting emboli flowing within a main vessel from entering first and second side branch vessels, including the steps of advancing an emboli deflection device through the first side branch vessel and into the main vessel; and manipulating the deflection device such that it covers the ostia of each of the first and second side branch vessels, wherein the deflection device permits blood flow from the main vessel into each of the first and second side branch vessels, but deflects emboli from entering the first and second side branch vessels without obstructing the lumen of the main vessel.

In some embodiments, the methods disclosed herein could be performed prior to, such as within 24 hours prior to a procedure such as a coronary angioplasty procedure, a cardiac valve replacement procedure, an aortic repair procedure, a cardioversion procedure, or in a patient having a cardiac arrhythmia.

In some embodiments, disclosed herein is a method of deflecting emboli flowing within a main vessel from entering first and second side branch vessels, including the steps of advancing an emboli deflection device into the main vessel; and manipulating the deflection device such that it covers the ostia of each of the first and second side branch vessels, wherein the deflection device permits blood flow from the main vessel into each of the first and second side branch vessels, but deflects emboli from entering the first and second side branch vessels without obstructing the lumen of the main vessel.

Also disclosed herein is a method of deploying an embolic deflector, comprising the steps of: providing an elongate, flexible tubular body, having a proximal end, a distal end, and a central lumen; the central lumen containing a deflector having a first end and a second end; advancing the distal end of the tubular body through a side branch vessel and into a main vessel; and advancing the deflector distally relative to the tubular body, such that the first end of the deflector extends from the tubular body within the main vessel in an upstream blood flow direction of the main vessel, and the second end of the deflector extends within the main vessel in a downstream blood flow direction of the main vessel from the tubular body. In some embodiments, at least one of the first and second ends of the deflector comprises radiopaque markers thereon. In some embodiments, advancing the distal end of the tubular body through a side branch vessel is accomplished using fluoroscopy.

Also disclosed herein is a method of establishing a seal between an embolic deflector and a main vessel wall, comprising the steps of: providing an embolic deflector assembly, having an elongate flexible shaft and an embolic deflector on a distal end of the shaft, the deflector movable between an axial orientation and a transverse orientation with respect to the shaft; advancing the deflector through a side branch vessel and into a main vessel while the deflector is in the axial orientation; converting the deflector to the transverse orientation within the main vessel; and applying traction to the shaft to bring the deflector into sealing engagement with a wall of the main vessel surrounding the opening to the side branch vessel. In some embodiments, applying traction to the shaft further comprises bringing the deflector into sealing engagement with a wall of the main vessel surrounding the openings to at least side two branch vessels. Applying traction to the shaft can include manipulating a torque control, in some embodiments.

In another embodiment, disclosed herein is a method of establishing and maintaining for a desired time, a seal between an embolic deflector and a main vessel wall, comprising the steps of: providing an embolic deflector assembly, having an elongate flexible shaft and an embolic deflector on a distal end of the shaft, the deflector movable between an axial orientation and a transverse orientation with respect to the shaft; advancing the deflector through a side branch vessel and into a main vessel while the deflector is in the axial orientation; converting the deflector to the transverse orientation within the main vessel; applying traction to the shaft to bring the deflector into sealing engagement with a wall of the main vessel surrounding the opening to the side branch vessel; and maintaining the traction. In some embodiments, the application of traction is maintained by applying frictional forces to the elongate flexible shaft, or by actuating a locking mechanism operably connected to the shaft.

In some embodiments, described herein is a method of removing an embolic deflection device having an elongate, flexible shaft extending through a side branch vessel and a deflector at the distal end of the shaft positioned within a main vessel, the deflector comprising a first portion extending in a first longitudinal direction within the main vessel and a second portion extending in a second longitudinal direction within the main vessel from a patient. The method can be accomplished by drawing the deflector proximally into the distal end of a tubular body such that the first portion advances towards the second portion; and proximally retracting the deflection device through the side branch vessel and from the patient. In some embodiments, the tubular body is a sheath surrounding the elongate flexible shaft. Prior to drawing the deflector proximally, the elongate flexible shaft and tubular body can be, in some embodiments, advanced into the lumen of the main vessel.

Also disclosed herein is a temporary emboli diversion device that includes an elongate, flexible shaft, having a proximal end and a distal end; and a deflector on the distal end. The deflector can have a length extending between a first end and a second end and a width extending between a first side and a second side. The deflector can be convertible between a folded configuration in which both the first end and the second end point in the distal direction, and a deployed configuration in which the first and second ends point in lateral directions. In some embodiments, the first end and the second end of the device can include radiopaque markers thereon.

Also disclosed herein is a temporary emboli diversion device, including an elongate flexible tubular body, having a proximal end, a distal end, and at least one lumen extending therethrough; and an elongate, flexible shaft, axially movably extending through the lumen; and a deflector carried by the shaft, the deflector movable between a first configuration for positioning within the lumen and a second configuration for deployment; wherein the deflector in the second configuration comprises a length measured transverse to the shaft which exceeds a width measured perpendicular to the length.

In another embodiment, disclosed is a temporary emboli diversion device, comprising an elongate flexible tubular body, having a proximal end, a distal end, and at least one lumen extending therethrough; an elongate, flexible shaft, axially movably extending through the lumen; and a deflector carried by the shaft, the deflector movable between a first configuration for positioning within the lumen and a second configuration for deployment; the deflector comprising a flexible frame extending around the periphery of the deflector, a membrane attached to the periphery of the deflector, and a suture loop encircling a portion of the flexible frame in at least one location on the periphery of the deflector.

Another embodiment of a temporary emboli diversion device can comprise an elongate flexible tubular body, having a proximal end, a distal end, and at least one lumen extending therethrough; an elongate, flexible shaft, axially movably extending through the lumen; and a deflector carried by the shaft, the deflector comprising first and second transversely biased lobes, each lobe having a medial end carried by the shaft and a lateral end.

Yet another embodiment of a temporary emboli diversion device can comprise an elongate, flexible shaft, having a proximal end and a distal end; a deflector carried by the shaft, the deflector having only a single plane of symmetry; wherein the shaft lies within the plane of symmetry.

Still another embodiment of a temporary emboli diversion device includes an elongate, flexible shaft, having a proximal end, a distal end and a longitudinal axis; a first porous lobe attached to the distal end of the shaft, the first porous lobe deflectable between an axial orientation and a lateral orientation; and a second porous lobe attached to the distal end of the shaft, the second porous lobe deflectable between an axial orientation and a lateral orientation. In some embodiments, the first porous lobe and the second porous lobe comprise pores having a size of no greater than 100 micrometers.

Another embodiment of a temporary emboli diversion device comprises an elongate flexible tubular body, having a proximal end, a distal end, and at least one lumen extending therethrough; an elongate, flexible shaft, axially movably extending through the lumen; a deflector carried by the shaft, the deflector extending transversely with respect to the shaft between a first end and a second end; and a first radiopaque marker carried by the first end and a second radiopaque marker carried by the second end.

A further embodiment of a temporary emboli diversion device includes an elongate flexible tubular body, having a proximal end, a distal end, and at least one lumen extending therethrough; an elongate, flexible shaft, axially movably extending through the lumen; a deflector carried by the shaft, the deflector extending transversely with respect to the shaft and having a length which exceeds its width; and a torque control carried by the shaft.

In another embodiment, disclosed is an embolic deflector comprising an elongate, flexible shaft, having a proximal end and a distal end; and a deflector, carried on the distal end of the shaft; wherein the deflector is curved in at least two axes such that it lacks radial symmetry with respect to a longitudinal axis of the shaft, and a peripheral edge of the deflector has a three dimensional configuration such that it conforms approximately to the interior surface of a non-spherical geometry of rotation, such as a cylindrical geometry of rotation in some embodiments, when the deflector is positioned in a main vessel and when the shaft extends through a branch vessel under traction.

In another embodiment, disclosed is a method of protecting the cerebral circulation from embolic debris, comprising the steps of: advancing a deflector into the aorta in the vicinity of the ostium to the left common carotid artery while the deflector is in a first, reduced profile configuration; deploying the deflector in the aorta, into a second configuration which is concave in the direction of the ostium; and transforming the deflector into a third configuration, which is concave towards a central axis of the aorta.

In another embodiment, disclosed herein is a method of reducing the risk of emboli entering the cerebral circulation as a consequence of an index procedure in the heart. The method includes the steps of introducing an elongate, flexible shaft into the vasculature at a point other than a femoral artery, the shaft carrying a deflector thereon; positioning the deflector in the aorta such that it spans the ostium of at least the brachiocephalic and left common carotid arteries; introducing an index procedure catheter into the femoral artery; advancing the index procedure catheter across the thoracic aorta and to a treatment site in the heart; conducting the index procedure in the heart; removing the index procedure catheter from the patient; and removing the deflector from the patient. In some embodiments, the index procedure could be a transcatheter aortic valve implantation, a balloon aortic or mitral valvuloplasty, a mitral or aortic valve replacement, a heart valve repair, or a coronary angioplasty. In some embodiments, the deflector is introduced into the vasculature via, for example, the ulnar, radial, brachial, axillary, subclavian, or brachiocephalic arteries, or into the aorta. In some embodiments, the deflector additionally spans the ostium of the left subclavian artery. The deflector could be introduced through a delivery catheter having a size of no greater than about 6 French. In some embodiments, the deflector comprises an atraumatic surface for contacting the wall of the aorta. In some embodiments, the removing the deflector step is accomplished no sooner than 1, 2, 3, 4, 5, 10, 15, 20, 30, 40, 50, 60 minutes, or more following completion of the index procedure.

Also disclosed herein is a method of reducing the risk of emboli entering the cerebral circulation as a consequence of an index procedure in the heart, or in another vessel, such as the aorta. The steps include introducing an elongate, flexible shaft into the aorta via the brachiocephalic artery, the shaft carrying a deflector thereon; positioning the deflector in the aorta such that it spans the ostium of at least the brachiocephalic and left common carotid arteries, and the left subclavian artery in some embodiments; conducting an index procedure on the heart; and removing the deflector from the patient. The index procedure could be conducted, in some cases, via open surgical access, transapical access, or thoracotomy access to a site on the heart.

BRIEF DESCRIPTION OF THE DRAWINGS

The invention will now be explained and other advantages and features will appear with reference to the accompanying schematic drawings wherein:

FIGS. 14A-K and 15A-15L depict various embodiments of embolic deflectors in plan view (14A-G), phantom plan view (14H-K) and side view (15A-L).

DETAILED DESCRIPTION OF THE PREFERRED EMBODIMENTS

Figure 1:
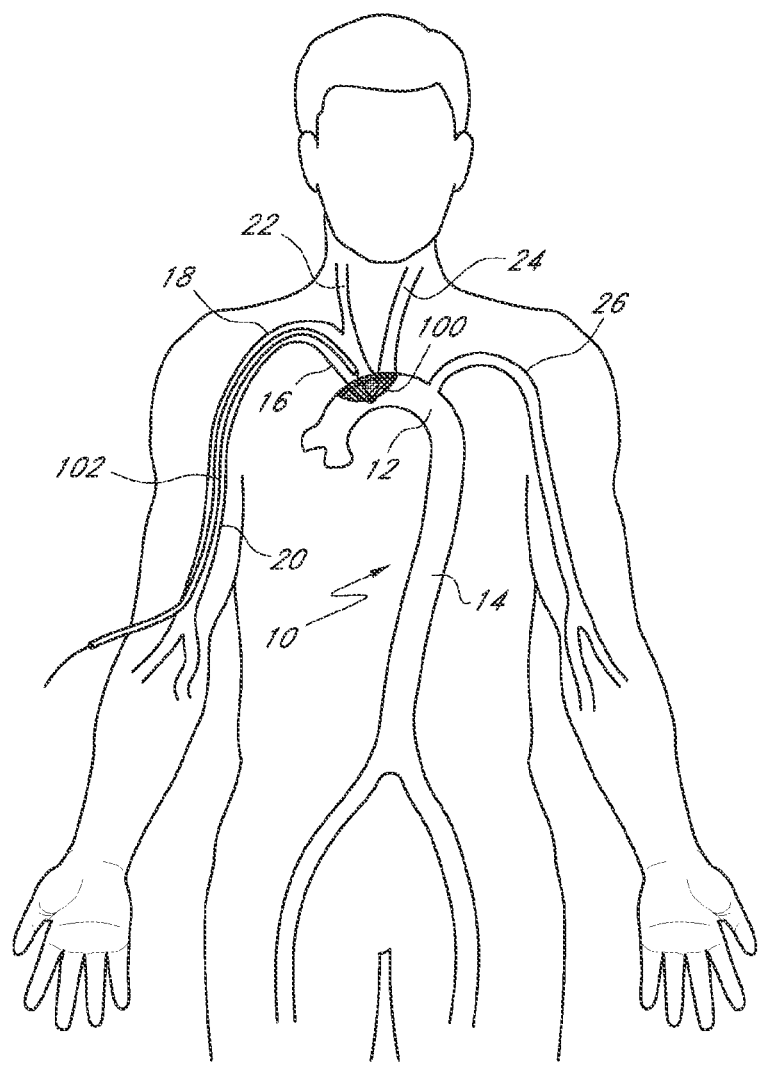
FIG. 1 depicts brachial artery insertion of an embolic deflector, according to one embodiment of the invention.

Disclosed herein are embolic protection systems that includes a deflector, along with associated deployment and removal systems, that can advantageously prevent emboli above a predetermined threshold size from entering the cerebral vasculature that may be dislodged, such as during an index procedure, such as an operative procedure. As such, potentially life-threatening transient ischemic attacks or embolic strokes can be prevented. Conventional embolic filters are primarily configured to capture, retain and retrieve embolic material. In contrast, deflectors as disclosed herein are configured to deflect or otherwise divert embolic material to a location downstream (relative to the direction of blood flow in the vessel in which the deflector is deployed) of the deployed location of the deflector to a less critical region of the body rather than the brain and other tissues perfused by the carotid and vertebral arteries. Once downstream, the emboli can be acted upon by physiologic anticoagulation mechanisms and/or externally administered anticoagulants. When in use, the emboli need not necessarily physically come into contact the embolic deflection device for the device to be effective, so long as the emboli are prevented from travelling through the deflector and are instead diverted downstream as noted above. In some embodiments, the deflector can be deployed in the aortic arch over the ostia of the brachiocephalic and the left common carotid arteries. In some embodiments, the deflector can be deployed in the aortic arch over the ostia of the brachiocephalic, left common carotid, and the left subclavian arteries. The right common carotid artery and the right subclavian artery normally branch off the brachiocephalic artery. The right vertebral artery normally branches off the right subclavian artery, while the left vertebral artery normally branches off the left subclavian artery. While the deflector is configured to deflect emboli greater than a pre-determined size, such as 100 microns for example, into the descending aorta, the deflector is also preferably configured to be sufficiently porous to allow adequate blood flow through the ostia of the vessels in which the deflector may contact, such as the brachiocephalic, left common carotid, and/or left subclavian arteries, so as to sufficiently maintain perfusion to the brain and other vital structures.

The method advantageously allows for deflection of emboli flowing within a main vessel, such as the aorta, from entering a side branch vessel, such as the brachiocephalic artery, left common carotid artery, and/or left subclavian artery while allowing deflection of the emboli further downstream in the main vessel (e.g., the aorta) perfusing less critical body organs and other structures, and allowing for lysis of the emboli via physiologic and/or pharmacologic declotting mechanisms. A side branch vessel as defined herein is a non-terminal branch vessel off a main vessel, such that the main vessel continues proximally and distally beyond the ostia of the side branch vessels. For example, the brachiocephalic artery, left common carotid artery, and left subclavian arteries are side branch vessels of the aorta, which continues distally toward the abdomen past the ostia of the aforementioned side branch vessels. This is in contrast to main vessels that can split (e.g., bifurcate) into terminal branch vessels such that the main vessel no longer exists distal to the ostia of the terminal branch vessels. One example of a main vessel that splits into terminal branch vessels is the abdominal aorta, which terminates distally subsequent to its bifurcation into the common iliac arteries.

In some embodiments, the deflector can be placed in a first axial, collapsed orientation through a first insertion site, such as an artery of an upper extremity that is distinct from a second insertion site, such as a femoral or contralateral upper extremity, for catheters and other devices used for a primary procedure. In some embodiments, the embolic deflector can be deployed with no greater than about a 6 French sheath, and can be readily placed using standard Seldinger technique. The device can be collapsed into its reduced crossing profile orientation through a loader, back loaded past the hemostasis valve of a sheath, and then advanced through the sheath into a first branch vessel, such as the brachiocephalic artery, and then into a main vessel, such as the aorta. Within the aorta, the deflector is expanded into an expanded transverse orientation once removed from the sheath, and is positioned across the ostia of one or more branch vessels to deflect emboli downstream (with respect to the direction of blood flow in the aorta) into the descending aorta.

In the expanded configuration, the deflector generally has a major axis with a length that is greater than the length along a transverse, or minor axis. As deployed within the vessel, the major axis is generally aligned in the direction of blood flow, such that a first end of the deflector residing on the major axis points in an upstream direction and a second, opposing end of the deflector also residing on the major axis points in a downstream blood flow direction.

A first end of the deflector can thus be aligned or permitted to self-align and can be secured in position extending upstream in the aorta covering, for example, the ostia of a branch vessel, such as the innominate artery. The deflector can also be configured to simultaneously have a second end extending downstream in the aorta to cover the ostia of a second branch vessel (e.g., the left common carotid artery).

The embolic defector is able to be placed before the index procedure is begun and can remain in place, providing embolic deflection, until the procedure is completed, or for a shorter or longer period of time as clinically indicated. In some embodiments, the deflector has a very low profile in the aorta so that wires, catheters, and sheaths can pass by it without interference. In some embodiments, the deflector is configured to deflect emboli greater than, for example, 100 microns in size away from the carotid arteries thus protecting the patient from potentially devastating neurological consequences of these emboli. The deflector can be designed so that one size fits all, or may be provided in a series of graduated sizes.

In some embodiments, a method of reducing the risk of emboli entering the cerebral circulation as a consequence of an index procedure in the heart or another blood vessel, such as the aorta, involves the following steps. First, an elongate, flexible shaft is inserted into the vasculature at a point other than a femoral artery, or in some embodiments a contralateral femoral artery from that of the insertion point for the index procedure. A deflector is then positioned in the aorta such that it spans the ostium of one, two, or more of the brachiocephalic, left common carotid, and left subclavian arteries. An index procedure catheter is then introduced into a femoral artery. The index procedure catheter is then advanced across the thoracic aorta to a treatment site in the heart or a blood vessel. The index procedure is then performed. Some non-limiting examples of index procedures include valve replacement procedures, including aortic and mitral valve replacement, including transcatheter aortic or mitral valve implantation, aortic or mitral valvuloplasty, including balloon valvuloplasty, heart valve repair, coronary angioplasty, or. coronary artery bypass grafting. Following completion of the index procedure, the index procedure catheter is removed from the patient. The deflector is then removed from the patient. In another embodiment, the method includes introducing an elongate, flexible shaft into the aorta, such as via the brachiocephalic artery, the shaft carrying a deflector thereon. The deflector is then positioned in the aorta such that it spans the ostium of one, two, or more of the brachiocephalic, left common carotid, and left subclavian arteries. An index procedure is then performed on the heart or other vessel, such as the aorta. The deflector can then be removed from the patient. The index procedure could be performed via open surgical access, a less invasive thoracoscopic approach, transapically, percutaneously, or even noninvasively (e.g., an external DC cardioversion) in some embodiments.

One embodiment of a method of using an embolic deflector to reduce the risk of emboli from entering the circulation during a Balloon Aortic Valvuloplasty (BAV) procedure will now be described. Wire access is gained through any appropriate access, such as the right radial or brachial artery and advanced to the ostium of the brachiocephalic artery. A 6 French Sheath with a dilator is then inserted over the wire. The sheath tip is positioned at the ostium of the brachiocephalic artery. An embolic deflector is inserted into the sheath and deployed in the aorta. The device positioning is confirmed with fluoroscopic imaging. A BAV catheter is inserted via the femoral artery. A Balloon Aortic Valvuloplasty catheter is advanced into the descending aorta, around the aortic arch passing by the deflector. The BAV catheter is then positioned across the aortic valve. The balloon is inflated and deflated against the stenotic and calcified aortic valve. The BAV catheter is then removed, passing by the embolic deflector during the retrieval process, through the femoral artery access site. The embolic deflector and sheath are removed from the radial or brachial artery.

One embodiment of a method of using an embolic deflector to reduce the risk of emboli from entering the circulation during a Transcatheter Aortic Valve Implantation (TAVI) will now be described. Wire access is gained through the right radial or brachial artery and advanced to the ostium of the brachiocephalic artery. A 6 French Sheath with a dilator is then inserted over the wire. The sheath tip is positioned at the ostium of the brachiocephalic artery. A deflector is inserted into the sheath and deployed in the aorta. The device positioning is confirmed with fluoroscopic imaging. Multiple wires and catheters are then used to assess the aortic valve and arch anatomy and to dilate the aortic valve prior to the deployment of the transcatheter aortic valve. These devices are inserted via the femoral artery and pass the deflector. The transcatheter aortic valve is then inserted via in a delivery system or catheter which is inserted via the femoral artery. A transapical or trans-septal approach could be employed in some embodiments. The TAVI catheter is advanced into the descending aorta, around the aortic arch passing by the deflector. The valve is then positioned and deployed in the native aortic valve. The TAVI catheter is then removed, passing by the deflector device during retrieval through the femoral access site. Once the TAVI catheter is removed, the deflector device and sheath are removed from the radial or brachial artery. Further details of replacement valves and methods of valve implantation that can be used with the deflectors described herein can be found, for example, in U.S. Pat. No. 7,618,446 to Andersen et al., U.S. Pub. No. 2008/0004688 to Spenser et al., U.S. Pat. Pub. No. 2007/0043435 to Seguin et al., U.S. Pat. Pub. No. 2008/0140189 to Nguyen et al., and U.S. Pat. Pub. No. 2008/0051807 to St. Goar et al., U.S. Pat. Pub. No. 2009/0062908 to Bonhoeffer et al., all of which are hereby incorporated by reference in their entireties.

Deployment of a deflector as described herein can be advantageous for a variety of applications. The applications may include use during a wide range of operative procedures, including but not limited to open cardiothoracic, mediastinoscopy, transapical, or percutaneous procedures. For example, the embolic deflector could be deployed prior to an angioplasty procedure, such as a balloon angioplasty or rotational atherectomy involving one, two, or more coronary arteries. The deflector could also be deployed prior to a heart valve procedure, such as an open, transapical, or percutaneous mitral or aortic valve replacement or repair or valvuloplasty procedure. In some embodiments, the deflector could be deployed prior to repair of an aortic aneurysm and/or dissection. In still other embodiments, the deflector could be deployed prior to electrical or pharmacologic cardioversion of an arrhythmia where there may be an increased potential risk of embolization following return to normal sinus rhythm post-cardioversion, such as in atrial fibrillation, atrial flutter, multifocal atrial tachycardia, ventricular tachycardia, ventricular fibrillation, or torsades de pointes for example. In some embodiments, the embolic deflector could be utilized in any index procedure involving the passage of catheters crossing the atrial septum, including cardiac ablation procedures of ectopic atrial or ventricular foci, leading to arrhythmias. Other examples of index procedures could include repair of shunt defects, including atrial septal defects, ventricular septal defects, patent foramen ovale, and Tetralogy of Fallot.

In some embodiments, the deflector is deployed within a patient no more than about 48 hours, 36 hours, 24 hours, 12 hours, 8 hours, 6 hours, 4 hours, 3 hours, 2 hours, 1 hour, or less prior to the index procedure. In some embodiments, the deflector is removed from a patient no sooner than 1, 2, 3, 4, 5, 10, 15, 20, 30, 40, 50, 60 minutes, or more following completion of the index procedure.

In some embodiments, deflector embodiments as disclosed herein could be deployed into the venous circulation, such as in the superior or inferior vena cava, for the prevention of pulmonary embolism.

In some embodiments, the deflector can be deployed for short-term or long-term protection against emboli even in when an operative procedure may not be contemplated, such as, for example, with a hypercoagulable state, cancer, atrial fibrillation, endocarditis, rheumatic heart disease, sepsis, including fungal sepsis, patent foramen ovale, atrial septal defect, ventricular septal defect, other arteriovenous shunt, or patients already having an implanted prosthetic device prone to emboli formation, such as having a prosthetic heart, left ventricular assist device, replacement mitral or aortic valve, and the like. For example, a patient may be on anticoagulant therapy for one, two, or more of the aforementioned conditions, but need to temporarily discontinue the medication for an upcoming procedure, or the medication may be temporarily contraindicated because of an acute bleed such as a gastrointestinal bleed, and thus be at risk for embolic stroke. A deflector can thus be deployed for the period of time in which the patient has discontinued their anticoagulation therapy, which may be more than about 12, 18, 24, 36, 48, 72 hours, or more. In other embodiments, the deflector can be configured for more long-term implantation, such as for at least about 1, 4, 6 or 8 weeks, or even more. However, in other more short-term applications, the deflector is deployed within the body for no more than about 24, 18, 12, 6, 4, 3, 2, 1 hour, or even less.

In some embodiments, the device may also be deployed into a position in which one edge is inside the brachiocephalic artery, covering the ostium of the right common carotid, and in which the opposite edge extends into the aortic lumen and covers the ostium of the left common carotid artery, leaving the brachiocephalic ostium substantially unobstructed by the deflector.

Referring now to FIG. 1, in one embodiment, a deflector 100 can be delivered via percutaneous or cut-down insertion into the right brachial artery 20, advanced to the right subclavian artery 18, and then is guided into the aortic arch 12. The deflector 100 can then be deployed and then pulled back under traction into position to cover the ostia of the brachiocephalic artery 16 (which may also be referred to herein as the innominate artery or the brachiocephalic trunk) and left common carotid artery 24. The deflector 100 deflects emboli during cardiovascular procedures, allowing the flow of blood through deflector 100 and into the cerebral circulation (carotid arteries) sufficient to maintain perfusion to the brain and other vital structures, while at the same time not permitting the passage of emboli into the cerebrovascular circulation of a size which could cause stroke. Also illustrated in FIG. 1 for anatomical reference is the descending aorta 14, right common carotid artery 22, aorta 10, and left subclavian artery 26.

Figure 2:
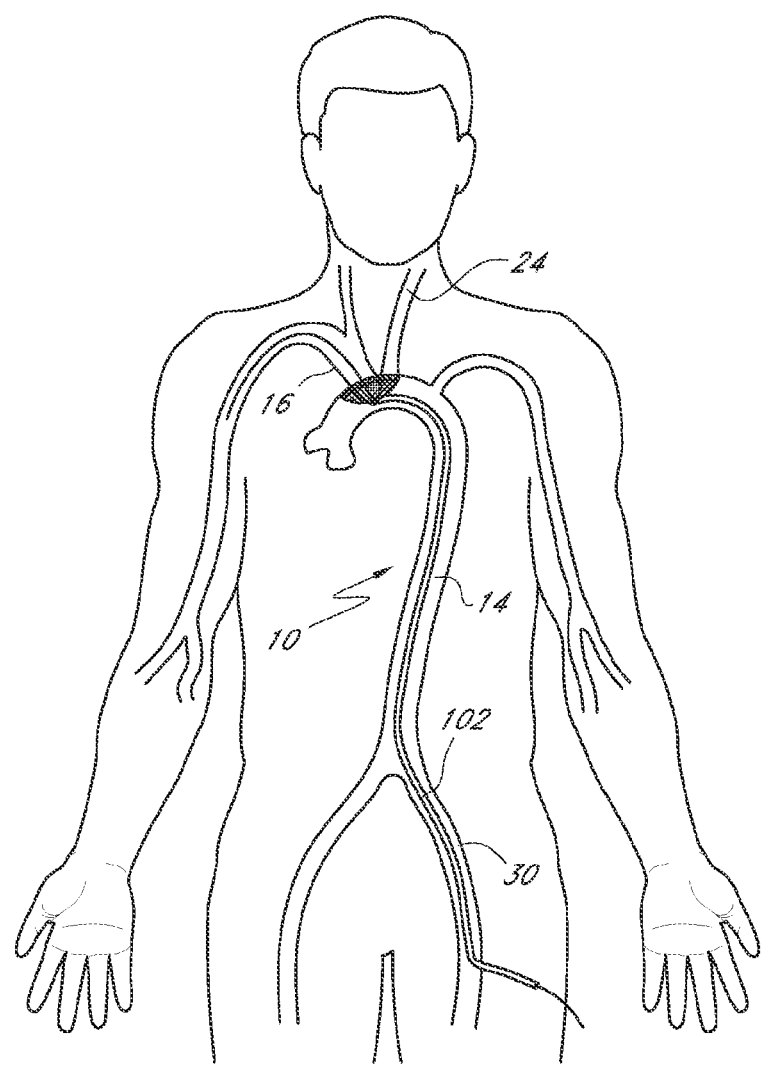
FIG. 2 depicts femoral artery insertion of an embolic deflector, according to one embodiment of the invention.

Referring now to FIG. 2, in one embodiment, the deflector 100 is delivered via percutaneous or cut-down insertion into a femoral artery (such as the left femoral artery 30) and is guided upstream from the descending aorta 14 into the aortic arch 12. After catheterization of the brachiocephalic artery 16, the device 100 is passed over a guidewire or through a lumen of a deployment catheter and brought into position and maintained under distal pressure covering the ostia of the brachiocephalic artery 16 and or the left common carotid 24 arteries, and additionally the left subclavian artery 26 (not shown) in some embodiments.

Referring now to FIGS. 3A-E, percutaneous access to the circulation via an upper extremity (through any appropriate artery, such as the radial, ulnar, brachial, axillary, or subclavian artery) is performed and a guidewire is advanced into the aortic arch after exiting the innominate artery.

A delivery catheter 102 is thereafter advanced over the wire to position a distal end of the delivery catheter in or in the vicinity of the aorta. Additional details of the delivery catheter and other mechanical components will be provided below. In general, the delivery catheter comprises at least one central lumen for receiving the deflector therethrough. The crossing profile of the system may be minimized by providing a delivery catheter 102 which comprises only a single lumen tube, such as a single lumen extrusion. This delivery tube may be advanced over the guidewire into position within the aorta. The guidewire is then proximally retracted and removed from the delivery catheter, leaving the central lumen available to receive the deflection device therethrough.

Figure 3A:
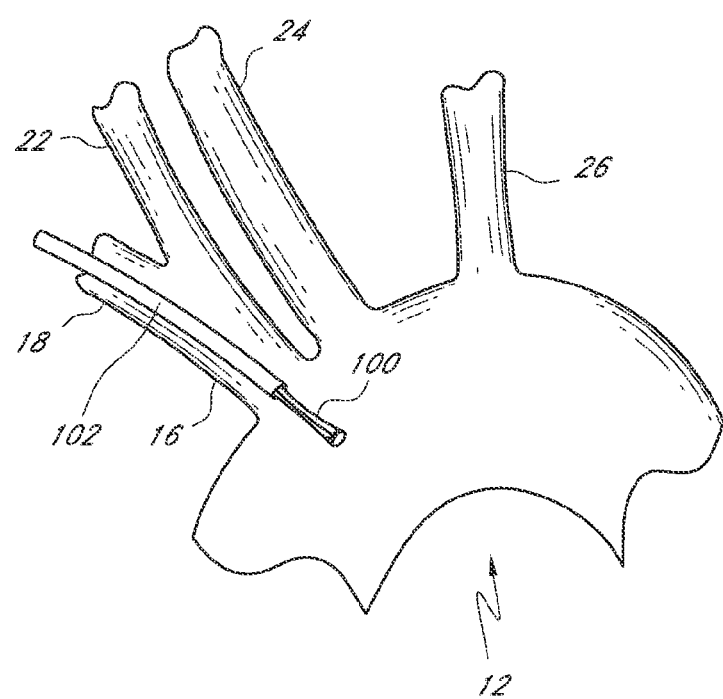
FIGS. 3A-E depict a method of deployment of an embolic deflector through the patient's right arm, thus allowing the deflector to be pulled back against the aortic wall to deflect emboli away from the cerebral vasculature, according to one embodiment of the invention.
Figure 3B:
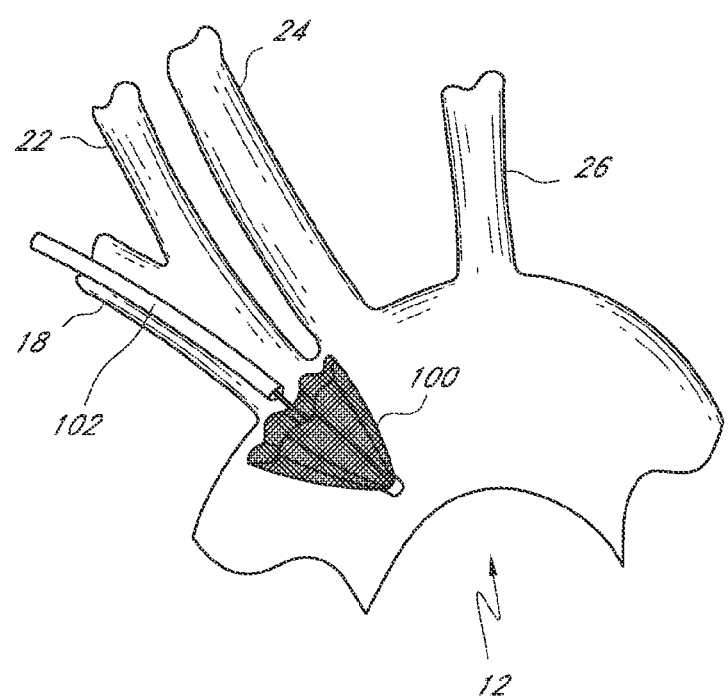
Figure 3C:
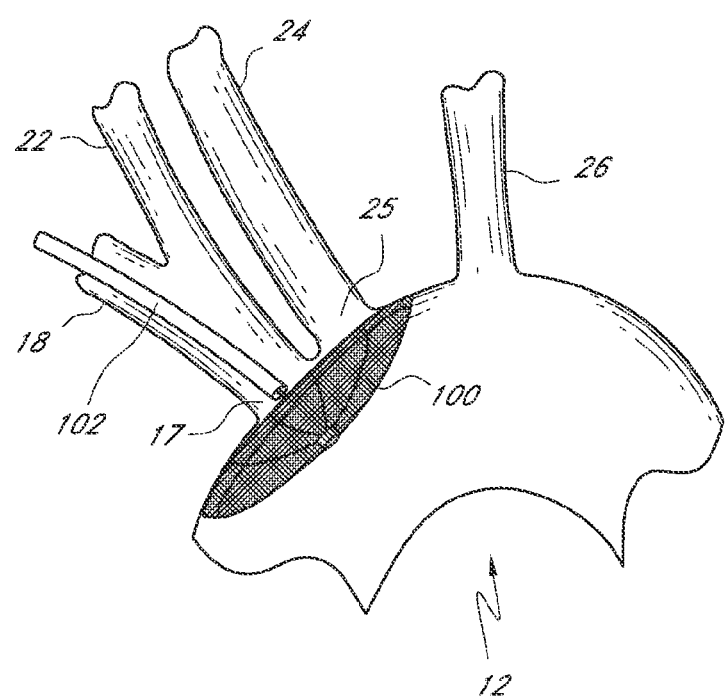
Figure 3D:
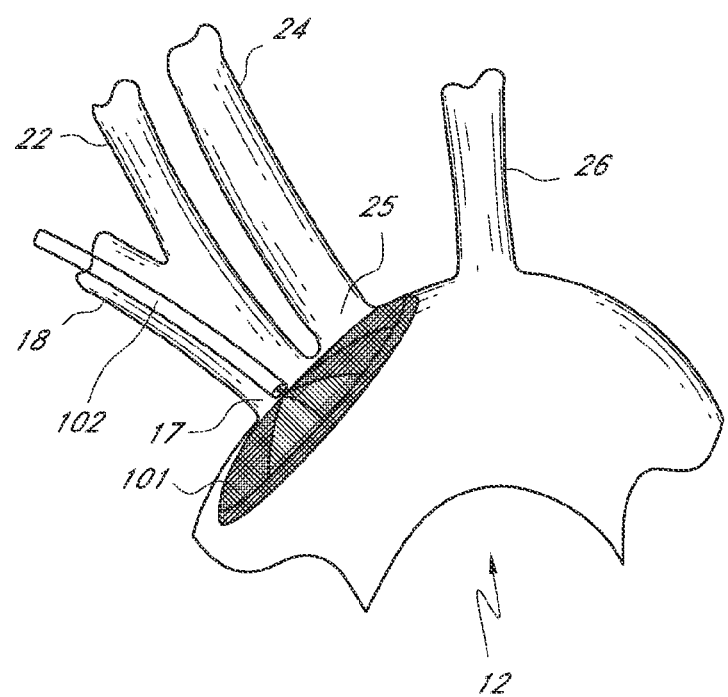
Figure 3E:
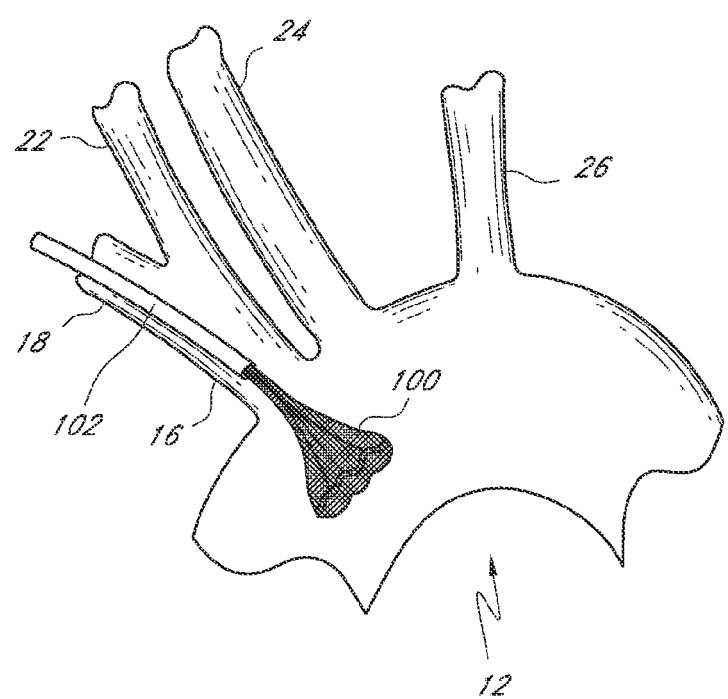

In the illustrated embodiment, the delivery catheter 102 is placed over the wire and guided into the aortic arch. The guidewire is retracted and the deflection device is axially distally advanced through the central lumen thereby exposing the device 100 to the aortic arch 12 bloodstream (FIG. 3A). The device 100 is then expanded in the aortic arch 12 (FIG. 3B). The device 100 is pulled back into position, covering the ostia 17 of the innominate artery 16 as well as the ostia 25 of the left common carotid artery 24 (FIG. 3C). The device 100 allows the passage of blood through to the carotid arteries 22, 24 while still deflecting emboli generated by aortic or cardiac surgery or other procedure away from these arteries, and downstream into the descending aorta. At the completion of the debris-producing concomitant procedure or following elapse of any other desired period of time, the device 100 is closed and withdrawn into the central lumen of deployment catheter 102 (FIG. 3E) to completely encapsulate it prior to removal from the arm access artery (not shown).

Figure 4A:
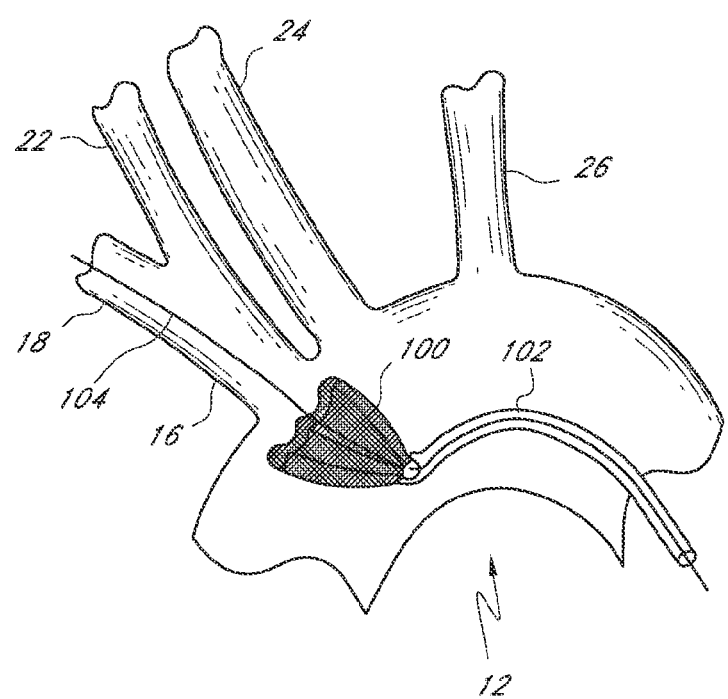
FIGS. 4A-F depict an alternative method of deployment of an embolic deflector through the femoral artery wherein the deflector is pushed against the aortic wall over the brachiocephalic and left common carotid ostia.
Figure 4B:
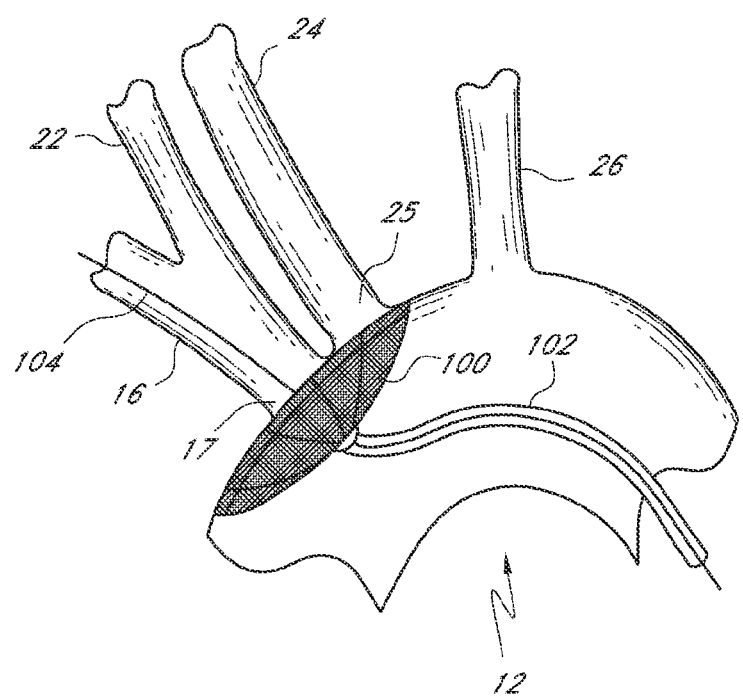
Figure 4C:
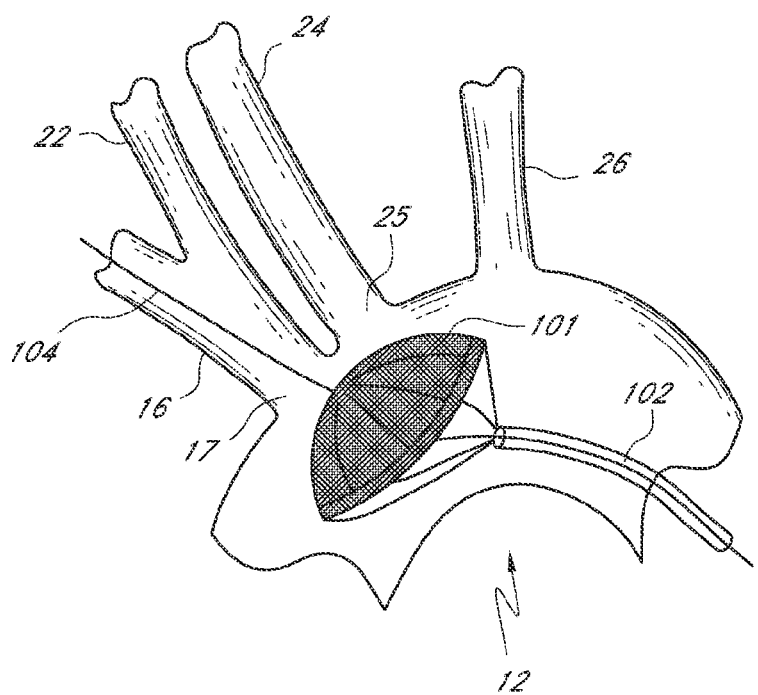
Figure 4D:
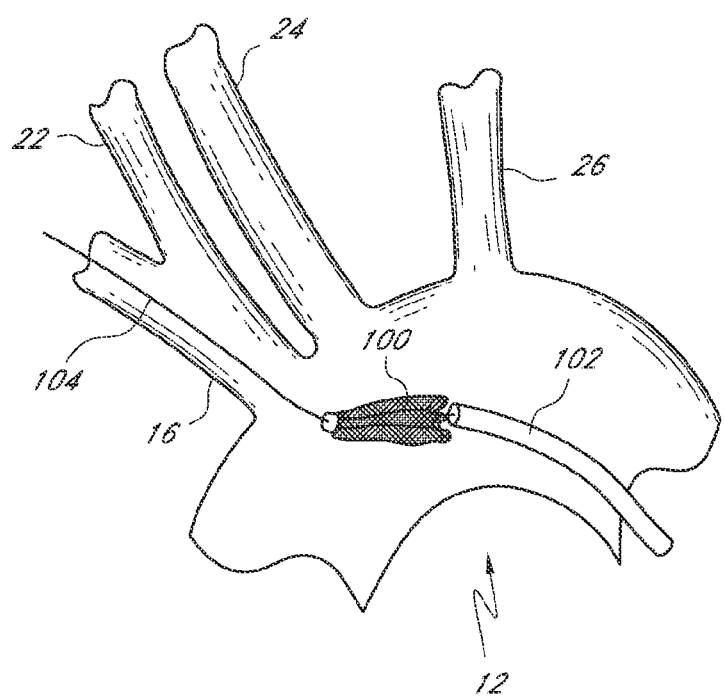
Figure 4E:
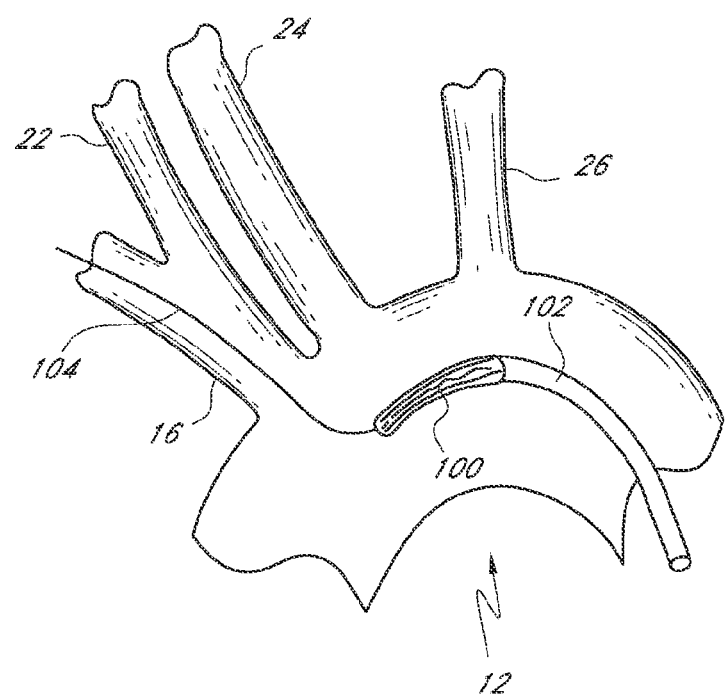
Figure 4F:
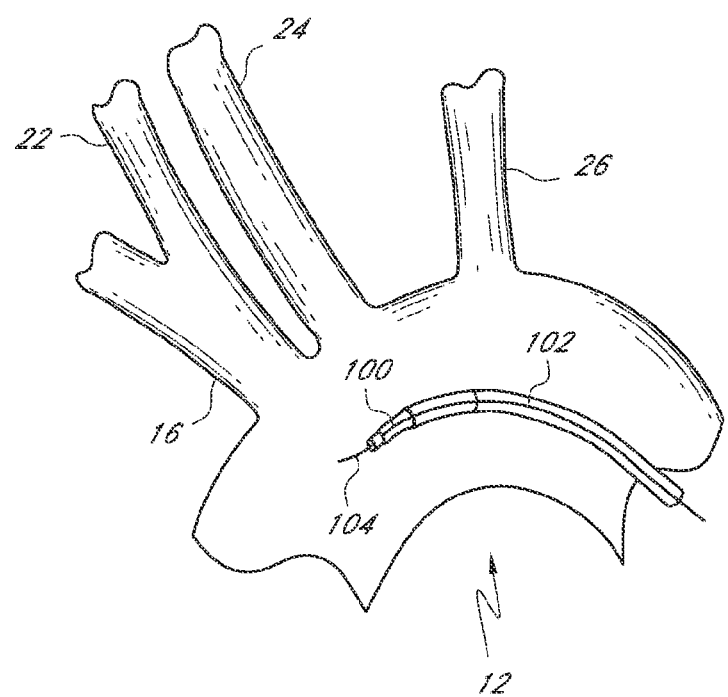

Referring now to FIGS. 4A-F, in another embodiment, the innominate artery 16 is catheterized with a wire 104 placed via femoral access. Over the wire, the deflector 100 deployment system is guided into position in the aortic arch 12, where the deflector is deployed, for example, by retraction of the sheath 102 (FIG. 4A). The device 100 is then pushed, over the wire 104 in the innominate artery 16, into position securely covering the ostia 17 of the innominate artery 16 and ostia 25 of the left common carotid artery 24 (FIG. 4B). As discussed above, the device 100 allows the passage of blood through to the carotid arteries 22, 24, but deflects emboli generated by aortic or cardiac surgery away from these arteries. At the completion of the debris-producing concomitant procedure or other period of time elapsed, the device 100 is closed by inverting the optional covering cap 101 (FIG. 4C), shown here by means of drawstrings. The device 100 is then collapsed (FIG. 4D) and withdrawn into a covering sheath 102 (FIG. 4E) to completely encapsulate it prior to removal from the leg access artery. Any trapped debris is enfolded within the closed cap 101, safely and securely within the covering sheath 102. The wire 104 and device 100 are then withdrawn from the femoral access.

In still other embodiments in which the ostia of three side branch vessels, such as the brachiocephalic artery, left common carotid artery, and left subclavian arteries are all to be covered by a deflector, an alternative deployment method would be through insertion of the vessel into the left upper extremity, such as the left radial, ulnar, brachial, axillary, or subclavian arteries. The deflector could be advanced into the aortic arch from the left subclavian artery, expanded, and then traction could be placed to create a seal with the aortic wall to cover the ostia of the three side branch vessels as discussed above.

Since deployment of the embolic deflection device via a femoral artery access can require placement of the deployment catheter across the thoracic aorta, this approach may be desirable for use in conjunction with heart procedures accomplished surgically, transapically, or via alternate access pathways that do not involve traversing the thoracic aorta with the primary procedure device.

In some embodiments, the device could also be used with open or thoracoscopic cardiac or aortic procedures. In these cases, the device could be placed in either manner described above, or via direct puncture or via guidance under imaging, such as fluoroscopy, into the aorta, brachiocephalic artery, right or left subclavian artery, or other suitable vessel if the arch were exposed. If it were placed directly, it would be pushed into place as with the femoral approach. Alternatively, any appropriate surgical, percutaneous, or endoscopic procedure may be employed to place the device.

During deployment as described above, in an embodiment in which the deflector is preloaded into the sheath 102 prior to advance to the treatment site, the deflector 100 may be locked in position relative to the sheath 102 using a rotating valve, torque control, or similar mechanism. The sheath 102 can then be held in position at the skin using, for example, a hemostat, clip, tape, Tegaderm™ or other adhesive film. The deflector 100 remains tethered by the shaft, and tensioned against the vessel wall by application of tractional force external to the patient. In some embodiments, a deployment system includes an intermediate biasing structure that reversibly locks the deflector 100 in position when a predetermined amount of tractional force is applied by a physician to place the deflector 100 in sealing contact against the vessel wall. The intermediate biasing structure could be, for example, a spring having a predetermined spring bias. Such an intermediate biasing structure could be advantageous in eliminating potential variability from physician in the amount of tractional force applied, to create an optimal seal as well as a safety feature to avoid damage to the intimal vessel wall or other structures. The deflector 100 and/or shaft may be elastic to accommodate movement or shifting during use, so as to maintain protection of the vasculature. The deflector 100 is preferably tethered to permit repositioning or removal at any time.

In some embodiments, mechanism of deflector expansion from the collapsed delivery configuration could include opening an umbrella (with or without struts), overlapping of opening lobes (blooming), opening of overlapping elements as in an iris, memory-restoration of a preformed shape, mushrooming, expansion of pores or cells, and release of supporting elements that form the peripheral shape with porous material stretched between.

The deflector may be transformed from the collapsed configuration to the open configuration using either passive or active mechanisms. In a passive expansion configuration, for example, the frame for the deflector is biased into the direction of the open configuration. The deflector is constrained within the delivery catheter 102, until the delivery catheter 102 is withdrawn proximally relative to the deflector, to expose the deflector within the aorta. At that point, the deflector expands radially outwardly under an internal bias. In one implementation, the sheath is held in a fixed axial position and the shaft is advanced distally therethrough to advance the deflector out of the distal end of the sheath. The opening bias may be provided by any of a variety of structures and materials, such as through the use of Nitinol, Elgiloy® or certain stainless steel alloys, as is known in the art. Alternatively, active opening mechanisms may include the use of one or more pull or push wires, or a rotational element, which can be actively manipulated to convert the deflector from the reduced profile to the enlarged profile.

In some embodiments, the method can be modified to account for patient anatomical abnormalities, such as abnormalities of the aortic arch. In some embodiments, the deflector 100 could cover the ostia of a single vessel, or a first deflector 100 could be sized to cover the ostia of a first vessel, and a second deflector 100 could be sized to cover the ostia of a second vessel. For example, some patients may have an aortic arch side branch vessel abnormality where the right common carotid artery and the left common carotid artery are both direct side branch vessels off the aortic arch, or the right and left common carotid artery bifurcate off a single side branch vessel off the aortic arch. The patient's vascular anatomy can be first determined, such as by angiography, CT angiography, MRI, doppler ultrasound, or other method. One, two, or more deflecting devices could be positioned at or near the ostia of one, two, three, or more side branch vessels (potentially more in patients with a double aortic arch) such that the end result is that all emboli larger than a predetermined size are prevented from reaching the brain including brainstem, eyes, or other critical structures perfused by the carotid and/or vertebral arteries.

Figure 4G:
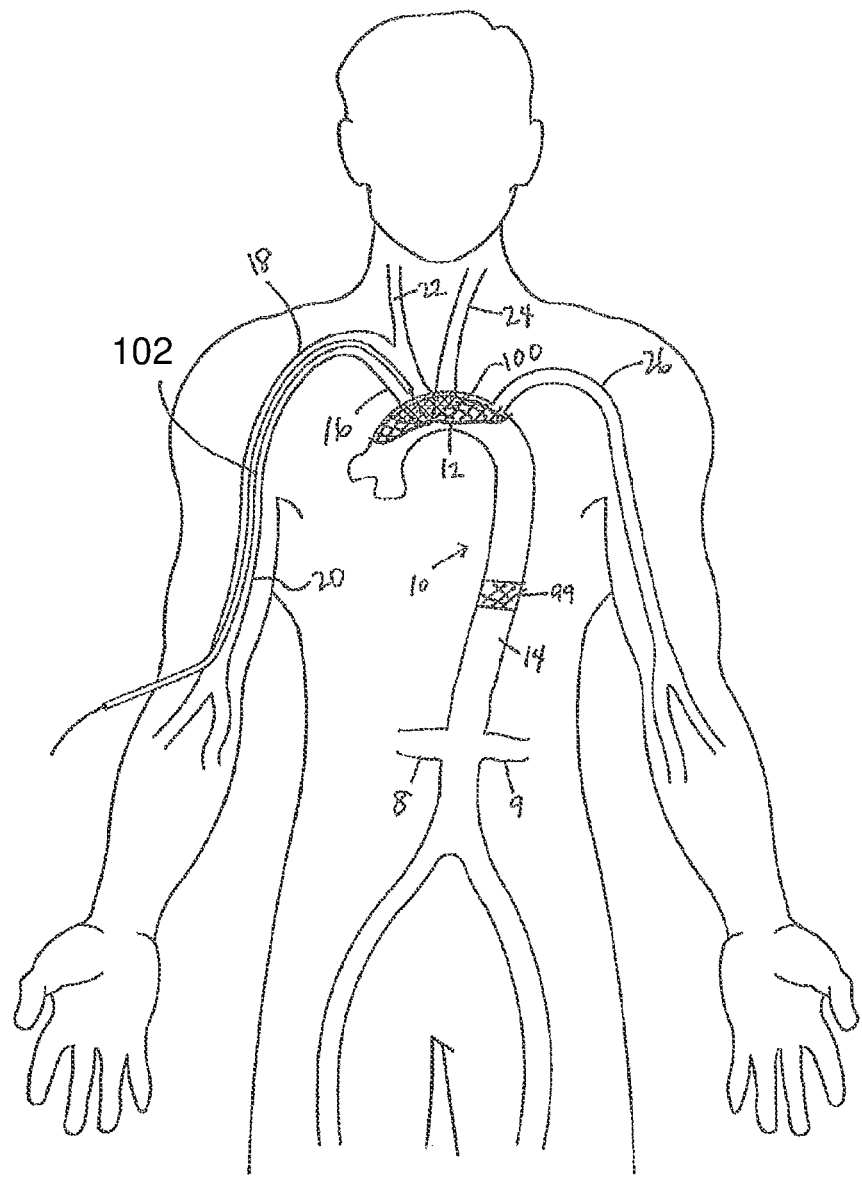
FIG. 4G illustrates an embodiment where an embolic deflector is used in combination with a filter spanning the aortic lumen and placed downstream of the left subclavian artery but upstream of the renal arteries.

In addition to deflectors 100 as described herein, conventional embolic protection devices including arterial and venous filters can also be sized and configured to be placed in a main vessel over the ostia of at least a first, second, or more side branch vessels and used with the methods disclosed herein, such as, for example, the brachiocephalic artery and the left common carotid artery as described above. In some embodiments, an embolic protection device sized and configured to span the aorta, such as the descending aorta, can be placed downstream of the deflector in the aortic arch to capture emboli before reaching the ostia of the renal arteries. FIG. 4G schematically illustrates a deployed deflector 100 that can cover the ostia of the brachiocephalic 16, left common carotid 24, and also the left subclavian artery 26. An adjunct embolic filter 99 can be placed in the aorta 10 downstream of the ostia of the left subclavian artery 26 but upstream of the ostia of the left 9 and right 8 renal arteries in order to trap emboli prior to potential embolization into the renal arteries 8, 9. In some embodiments, the embolic filter 99 could be a stand-alone filter as shown temporarily positioned and secured in the aorta via any desired mechanism, such as with anchors such as barbs, attached to a control line extending from the left or right femoral arteries or a right or left upper extremity artery, or tethered to the deflector 100 in some embodiments. The embolic filter 99 could then be removed from body following completion of the index procedure. Some examples of embolic protection devices including filters that can be used or modified for use with the methods described herein, as well as deployment and removal methods for those filters can be found, for example, in U.S. Pat. No. 4,619,246 to Molgaard-Nielsen et al., U.S. Pat. No. 5,634,942 to Chevillon et al., U.S. Pat. No. 5,911,734 to Tsugita et al., U.S. Pat. No. 6,152,946 to Broome et al., U.S. Pat. No. 6,251,122 to Tsukernik, U.S. Pat. No. 6,346,116 to Brooks et al., U.S. Pat. No. 6,361,545 to Macoviak et al., U.S. Pat. No. 6,375,670 to Greenhalgh et al., and U.S. Pat. No. 6,447,530 to Ostrovsky et al., all of which are hereby incorporated by reference in their entireties.

Figure 5:
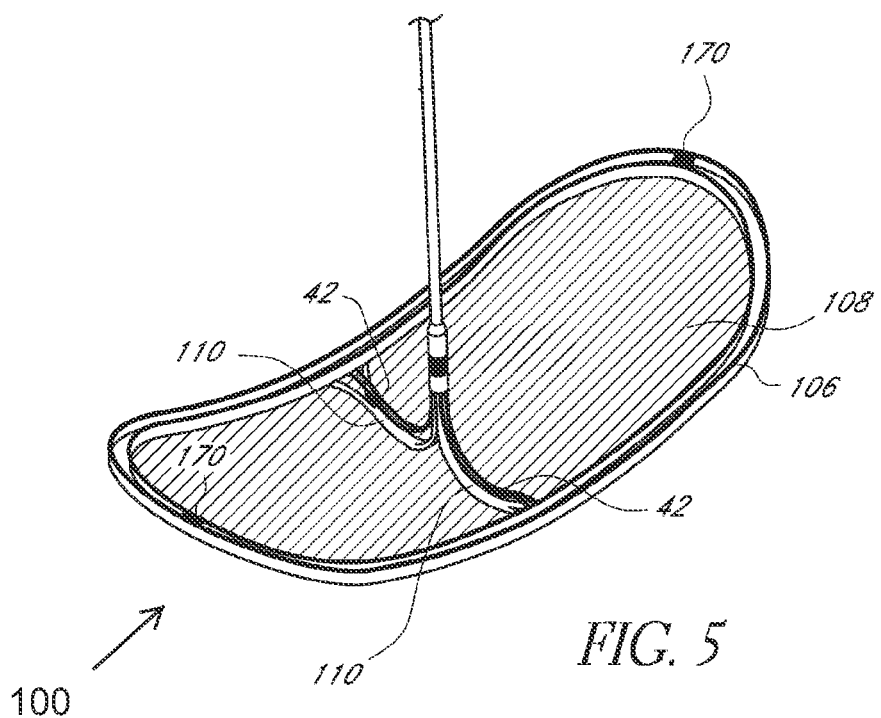
FIG. 5 illustrates a perspective view of one embodiment of an embolic deflector.

In some embodiments, an embolic deflector 100 includes the following components, as illustrated in FIG. 5. The deflector 100 can include a flexible frame 106 having a size sufficient to surround or support a deflection membrane across the ostia of both the brachiocephalic and left common carotid arteries while the deflector 100 is positioned in the aorta, specifically within the aortic arch region of the aorta. However, in other embodiments, the deflector 100 could be sized to cover the ostia of a single vessel, or a first deflector 100 could be sized to cover the ostia of a first vessel, and a second deflector 100 could be sized to cover the ostia of a second vessel. The frame 106 can be flexible, and take a wide variety of shapes to allow continuous or substantially continuous contact with the sidewall of the aortic arch lumen. The frame 106 surrounds or supports a membrane 108 which can be porous or include apertures such that the permeability of the membrane 108 allows the flow of blood into the cerebral circulation, while still deflecting and/or trapping emboli of a size which could cause a stroke.

The frame 106 is operably connected to an elongate, flexible shaft 300 to permit axial reciprocal movement of the deflector. In the illustrated embodiment, the frame 106 is connected to flexible shaft 300 by first and second struts 110. First and second struts 110 curve or incline radially outwardly in the distal direction, to assist in expanding the deflector 100 for deployment or alternatively contracting the deflector 100 for removal as it is drawn proximally into the deployment catheter 102. Three or four or more struts may be alternatively used. In some embodiments as illustrated, the deflector has only a single plane of symmetry, and the shaft 300 lies within that plane of symmetry (e.g., the plane of symmetry runs coaxial with the shaft 300 and extends across the minor (transverse) axis of the deflector).

The deflector 100 can also include one, two, or more control lines 42 which can assist in retrieving the deflector 100. The control line 42, which can be a loop of suture or other suitable material, could extend around the periphery of the membrane and be trapped by the membrane heat-bond or otherwise be secured to or near the periphery of the membrane. In some embodiments, one, two, or more suture loops pass through section(s) of membrane. Control line 42 assists in collapsing the device into the sheath 102 (not shown) during retrieval, by resisting the membrane from sliding along the frame 106. Control line 42 could pass over either the proximal or distal side of the frame. Alternatively, the membrane can be secured directly to the frame such that it does not slide on the frame upon retraction into the sheath, and the control lines can be omitted. The integrity of the bond will depend in part upon the materials of the frame and membrane. Depending upon those materials, any of a variety of bonding techniques may be utilized, such as adhesives, thermal bonding, or application of bonding or tie layers such as a polypropylene or FEP layer bonded to the frame which is heat bondable to itself and/or to the material of the membrane. The deflector 100 can also include one, two, or more radiopaque markers 170 that may be present on the lateral ends of the frame 106 and/or on the shaft 300 as shown, or in other clinically desirable locations. Further details and illustrations of various components of a deflector 100, in some embodiments, will be disclosed below.

Figure 6A:
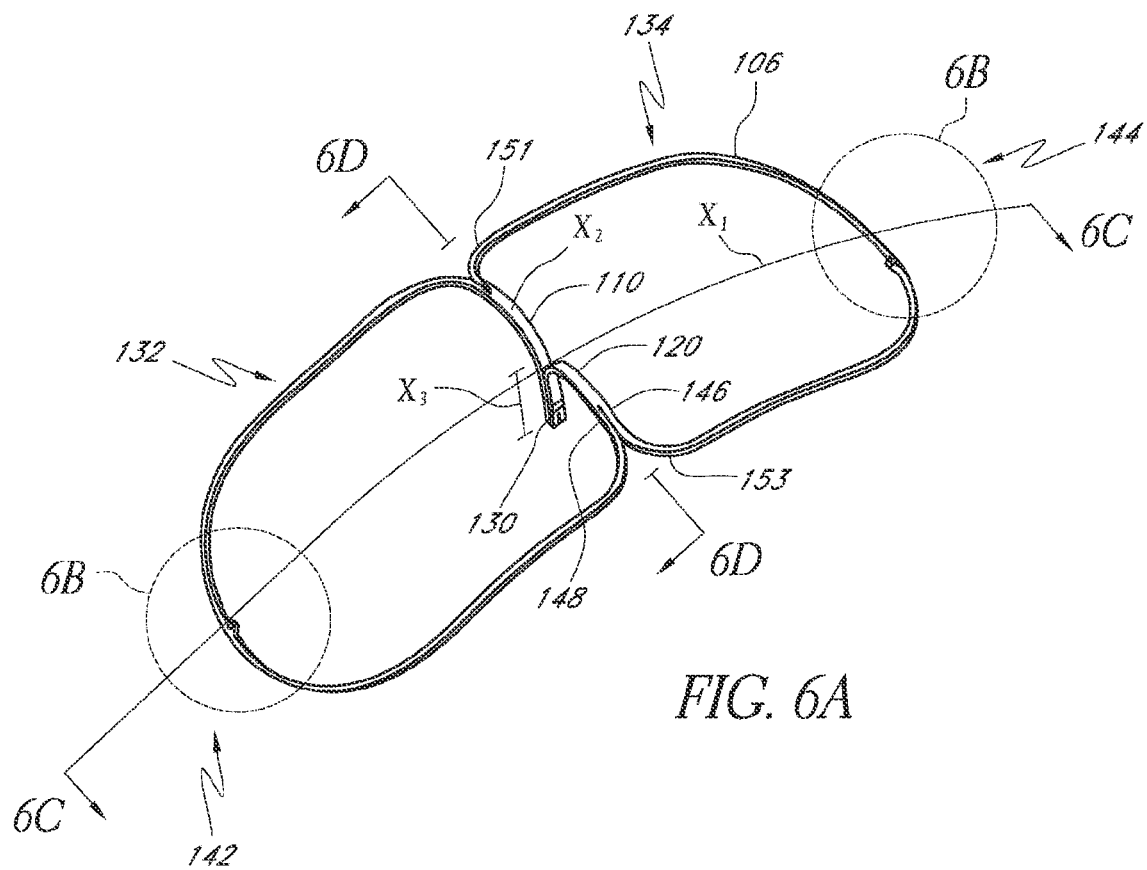
FIGS. 6A-B illustrate perspective views of a frame of an embolic deflector, according to one embodiment of the invention.

FIG. 6A illustrates a frame 106 of a deflector 100, according to one embodiment of the invention. The frame can be made of any appropriate biocompatible material, such as Nitinol, Elgiloy®, Phynox®, MP35N alloy, stainless steel, titanium, or a shape memory polymer that could be either nonbiodegradable or biodegradable, in some embodiments. Some examples of suitable polymers include poly (alpha-hydroxy acid) such as poly-L-lactide (PLLA); poly-D-lactide (PDLA), polyglycolide (PGA), polydioxanone, polycaprolactone, polygluconate, polylactic acid-polyethylene oxide copolymers, modified cellulose, collagen, poly (hydroxybutyrate), polyanhydride, polyphosphoester, poly (amino-acids), or related copolymer materials.

The frame 106 can be configured such that it is transformed from a first, low-profile reduced configuration during delivery to a second, expanded configuration while in use, and if necessary, back to the first low-profile reduced configuration for later removal. In some embodiments, as depicted in FIG. 6A, at least a substantial portion of the frame 106 is constructed from a single laser-cut piece of material. The frame 106 can also be assembled from two or more wires that are formed and welded or otherwise bonded together. In the illustrated embodiment, the frame includes a peripheral strut which is configured into two closed lobes bilaterally symmetrically positioned relative to the shaft 300. Additional struts may be included such as in a zig-zag configuration within each lobe.

While the frame 106 can be substantially flat from a first lateral end to a second lateral end, in some embodiments, the frame 106 is formed so that it is first biased into a proximally concave shape when in an unconstrained expansion, having a compound curvature to form a fitting seal against the aortic wall when it is deployed. In other words, the midpoint of the frame 106 where the shaft 300 is attached can be longitudinally offset along the axis of the shaft from the lateral ends of the frame 106, such as by at least 2, 4, 6, 8, 10, 12, 15 mm, or more, or between about 7-11 mm in some embodiments. The frame 106 can alternatively be formed by injection molding, cold forming, casting, or any other suitable method, or combination of methods, or the frame may be formed to assume the desired configuration upon inflation, heating, cooling, or exposure to body fluids.

The frame 106 can be defined as having a major axis (maximum length) X1 between a first lateral end and a second lateral end, and a minor axis (maximum width) X2 between a first side and a second side of the frame when laid flat and fully expanded, as well as a height X3 as illustrated in FIG. 6A. When laid flat, the frame can be sized to ensure coverage of both the brachiocephalic and left common carotid artery over a wide range of anatomies.

In some embodiments, the frame 106 is bilaterally symmetric and radially asymmetric, and has a major axis distance X1 that is at least about 100%, 110%, 120%, 130%, 140%, 150%, 175%, 200%, 225%, 250%, 275%, 300%, 325%, 350%, 400% or more relative to the minor axis distance X2. However, in other embodiments, the frame 106 may be radially symmetric like an umbrella, where the distances X1 and X2 are the same or substantially the same.

In some embodiments, the frame 106 has a length X1 of from about 40 mm to about 80 mm, such as from about 50 mm to about 70 mm, such as between about 56 mm to about 60 mm. The frame 106 can have a width X2 of from about 20 mm to about 30 mm, or from about 23 mm to about 27 mm in some embodiments. The frame 106 has a height X3 of from about 7 mm to about 11 mm, such as from about 8.5 to about 9.5 mm in some embodiments.

Still referring to FIG. 6A, the frame 106 can be defined by at least a first lobe 132 and a second lobe 134 biased in opposing radially outward directions, and intersected by struts 110, 120 meeting and becoming longitudinally offset from the frame 106 at junction 130. Struts 110, 120 and can be, in some embodiments, follow the minor axis X2 of the frame near the midpoint of the length along major axis X1 of the frame 106. The frame 106 can be attached to the shaft (not shown) via, for example, an interlocking feature cut into each of the central struts 110, 120 near junction 130. Complementary mating mechanical engagement structures can ensure sufficient strength for deployment, manipulation and retrieval of the device. However, heat welding, bonding, adhesives, or other attachments between the frame 106 and the shaft can also be utilized. In some embodiments, a segment of hypodermic tubing can be placed, such as crimped and/or bonded in place over the junction 130 for added stability.

As illustrated in FIG. 6A, first lobe 132 has a lateral end 142 and a medial end 148, while second lobe 134 also has a lateral end 144 and a medial end 146. Lobes 132, 134 also have a first side 151 and a second side 153, the distance between sides 151, 153 of which defines the width X2 of the frame 106. Lobes 132, 134 are movable between an axial orientation prior to delivery (best illustrated in FIGS. 11-12) to a transverse orientation following deployment in the vessel (best illustrated in FIG. 13). In the illustrated embodiment as well as others, the deflector 100 can be described as convertible between a folded configuration in which both the first end (e.g., lateral end 142) and the second end (e.g., lateral end 144) both point in the distal direction, and a deployed configuration in which the first and second ends 142, 144 point in lateral directions.

Still referring to FIG. 6A, the first lobe 132 is symmetric to, and encloses a surface area that is the same or substantially the same as a surface area enclosed by the second lobe 134. In other embodiments, the first lobe 132 is asymmetric to, and can enclose a surface area that is at least 10%, 20%, 30%, 40%, 50%, 75%, 100% greater, or more than the surface area enclosed by the second lobe 134. The lobular structure of the frame 106 allows the frame 106, in some embodiments, to have multiple thicknesses along the perimeter of the frame to provide varying stiffness as needed. The thinnest sections at each lateral end 142, 144 of each lobe 132, 134 respectively, can have a thickness of from about 0.30 mm to about 0.50 mm, or between about 0.38 mm and about 0.43 mm in some embodiments, can advantageously facilitate device collapse for delivery without permanent deformation of the frame, which could be a factor for working in a sheath profile such as 6 French, or no greater than 10, 9, 8, 7, 6, 5, 4, or less French in some embodiments. In some embodiments, the frame 106 includes 3, 4, 5, 6, 7, 8, or more lobes projecting radially outwardly from a central hub depending on the patient's particular anatomy and luminal sites to be protected by the deflector 100.

The deploy/collapse sequence emanates from the central struts 110, 120 at the point of contact with the wall surrounding the distal opening on deployment catheter 102 and continues to the radial ends of the lobes 132, 134 of the frame 106 as the struts slide in or out of the catheter. One benefit of this design is that the physician can visualize the respective lateral ends 142, 144 of the lobes 132, 134 as they deploy and radially expand, somewhat like a blooming flower. Another benefit is that the deflector 100 typically does not reach straight across the aorta or touch the wall of the lesser curvature of the aorta while deploying.

Thus, one half of the axial length of the deflector along longitudinal axis X1 may be greater than the diameter of the aorta in the vicinity of the ostium to the innominate artery, yet the deflector can be expanded or contracted within the aorta without contacting the wall on the inside radius of the thoracic aorta. This is because the lobes of the deflector advance radially outwardly as the shaft 300 is distally advanced relative to the deployment catheter.

Figure 6B:
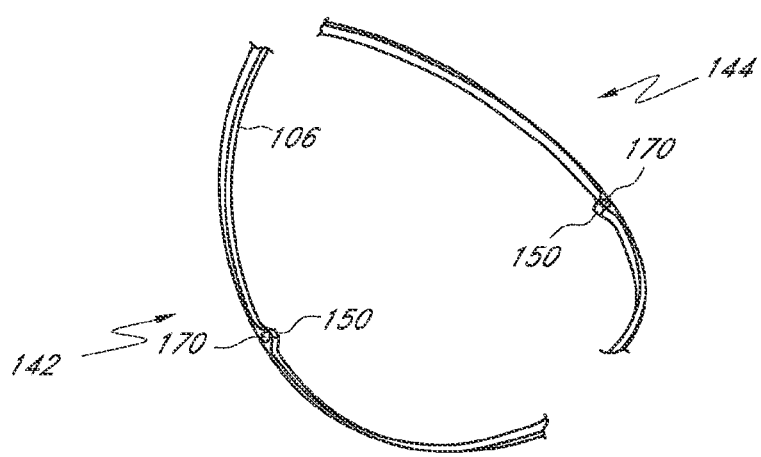

FIG. 6B is a close-up view of the respective lateral ends 142, 144 of the lobes 132, 134 highlighted in dashed circles 6B of FIG. 6A. As depicted in FIG. 6B, there are provided points of attachment 150 in the frame 106 for radiopaque (RO) markers 170 to be loaded. While the markers 170 could be located anywhere along the deflector 100, in some embodiments, the frame 106 includes one, two or more markers 150 on or centered about each lateral end 142, 144 as illustrated and one, two, or more markers on the shaft (not shown) for alignment with a radiopaque marker on the sheath. The radiopaque markers 170 on the frame lateral ends 142, 144 and on the shaft as well as the visibility of the frame 106 itself (if the frame 106 is at least somewhat radiopaque) aid in placement guidance.

In some embodiments, the radiopaque marker elements 170 are made of a metal or a metal alloy, such as, for example, one or more of Nitinol, Elgiloy®, Phynox®, MP35N, stainless steel, nickel, titanium, gold, rhenium, tungsten, palladium, rhodium, tantalum, silver, ruthenium, and hafnium. The marker element could be a 90% platinum and 10% iridium alloy in one particular embodiment. The radiopaque markers 170 disposed on the frame 106 or other portions of the deflector 100 may be welded, plated to the frame surface, painted thereon, dyed, applied as a wire wrap or coil, or any other suitable technique that allows for radiopaque marking. The position of the markers 170, in some embodiments, may be offset from the major axis of the frame to permit optimal folding of the frame 106.

Figure 6C:
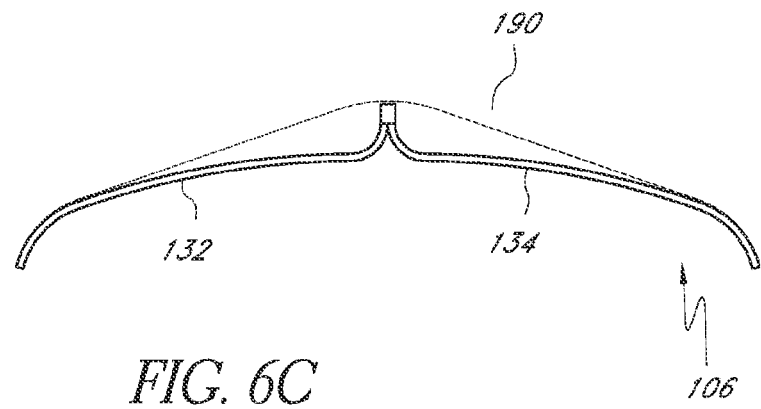
FIG. 6C is a longitudinal cross-sectional view of the embolic deflector of FIG. 6A, through line 6C-6C.

FIG. 6C is a longitudinal cross-sectional view of the embolic deflector of FIG. 6A, through line 6C-6C of FIG. 6A. As illustrated, the longitudinal cross-section of the frame 106 of the deflector generally follows an arc 190 about its longitudinal axis. The arc 190 is defined as a best-fit curve having a constant radius of curvature, as illustrated in FIG. 6C. The actual device will not necessarily conform precisely to a constant radius curve. In some embodiments, the radius of curvature of the best-fit curve 190 of the longitudinal cross-section of the deflector frame 106 is within the range of from about 0.5 inch to about 6 inches, or from about 1 inch to about 3 inches.

Figure 6D:
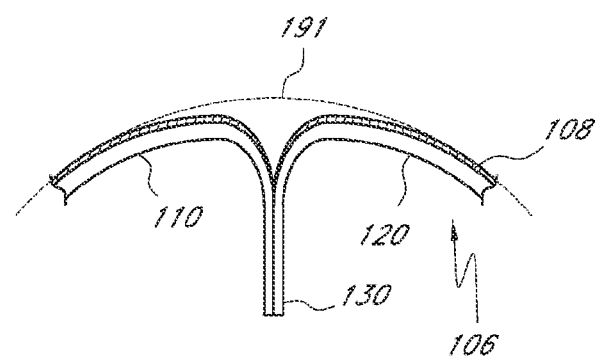
FIG. 6D is a transverse cross-sectional view of the embolic deflector of FIG. 6A, through line 6D-6D.

FIG. 6D is a transverse cross-sectional view of the embolic deflector of FIG. 6A, through line 6D-6D of FIG. 6A.

Similar to that of the longitudinal cross-section of the frame 106 discussed above, in some embodiments, the transverse cross-section of the membrane 108 (or frame 106) can be approximated by a best-fit curve 191 having a constant radius of curvature, as illustrated in FIG. 6D. In some embodiments, the radius of curvature of the best-fit curve 190 of the longitudinal cross-section of the membrane 108 is generally within the range of from about 0.2 inches to about 2.0 inches, or from about 0.4 inches to about 1 inch.

Thus, in some embodiments, a cross-section of the deflector can be said to follow a best-fit curve about a first axis and a second axis, such as both its transverse and longitudinal axes. In some embodiments, the radius of curvature of the best-fit curve 190 of the longitudinal cross-section of the frame 106 is at least about 100%, 150%, 200%, 400%, 500%, or more of the radius of curvature of the best-fit curve 191 of the transverse cross-section of the membrane 108. In part due to its geometry as described maintaining a concave bias in a proximal direction when fully expanded, the deflector advantageously creates a seal along a vessel well, such as the aortic arch, for positioning over the ostia of the brachiocephalic and the left common carotid arteries.

In other embodiments, the deflector can be said to follow a best-fit curve about only one of its transverse and longitudinal axes. In some embodiments with a different configuration, a cross-section of the frame or membrane may not follow a best-fit curve along either axis.

In all of the foregoing illustrations, the deflector is illustrated as it would appear in an unconstrained expansion. In vivo, it is intended that the flexibility of the deflector be sufficient that it can conform (i.e. bend) to the interior wall of the native vessel, under relatively mild proximal traction on the shaft 300, without deforming the configuration of the native vessel. Thus, the periphery of the frame is configured such that along its entire length or at least about 90% of the length of the frame will lie in contact with the inner wall of the vessel. For this reason the ends 142 and 144 of the deflector reside on the apexes of radiused axial ends of the deflector. The radiused ends are additionally curved in the device proximal direction as can be seen in FIGS. 5 and 6A through 6C, for example, to provide a generally boat shaped construct. This allow the deflector to reside within a cylindrical structure and contact the inner wall of the cylinder along substantially the entire length of the frame (the entire peripheral edge of the deflector), thereby enclosing a trapped space beneath (on the proximal side of) the deflector.

The aspect ratio of the deflector may therefore be optimized to the intended anatomy in which the deflector is to be used. In one implementation of the invention, the length of the deflector is approximately 2.3 inches and the width is approximately 0.82 inches. The radius of curvature of the ends of the deflector is about 0.41 inches. Thus, the radius of curvature of the ends of the deflector is approximately ½ the width of the deflector. In general, the radius of curvature of the ends of the deflector will be ½ of the width of the deflector±50%, preferably ±20%, in many embodiments ±10%, and, in one particular embodiment, ±2%.

In some embodiments, the frame 106 is configured for long-term implantation and embolic protection. As such, the frame 106 may include a plurality of anchors, such as barbs that can be located anywhere along the length of the frame, such as at the lateral ends. The shaft in such instances can be detachable from the frame upon implantation. In some embodiments, it may be desirable for the deflector 100 to be either partially or fully biodegradable over a period of time in which the patient may be at a lesser risk for continued embolic formation, such that manual removal of the deflector 100 may advantageously not be necessary. As such, temporary embolic deflector devices could either be configured for manual removal as described elsewhere herein, or biodegradable in other embodiments.

Figure 7:
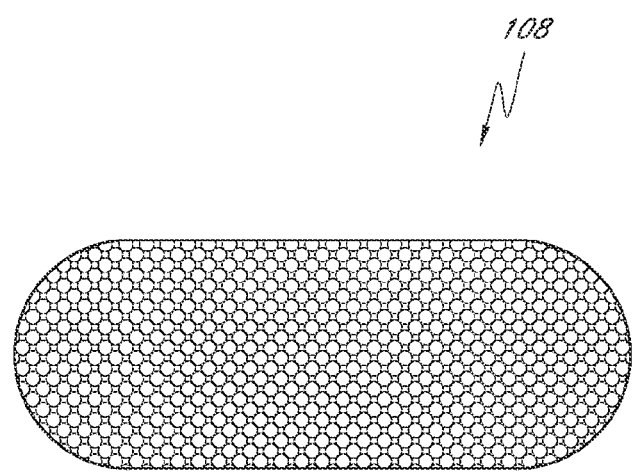
FIG. 7 illustrates a schematic view of a membrane portion of an embolic deflector, according to one embodiment of the invention.

FIG. 7 illustrates one embodiment of a membrane 108 of the deflector 100. The membrane 108 is configured to have a porous surface as to allow for blood flow sufficient to perfuse the brain and other important structures served by the carotid and vertebral arteries, but also deflects emboli greater than a size of which is likely to cause an embolic stroke of clinical significance. In some embodiments, the membrane 108 has pores that are no more than about 200 μm, 175 μm, 150 μm, 125 μm, 100 μm, 75 μm, 50 μm, or even less in size. In some embodiments, the membrane 108 has pores that are no more than about 100 micrometers in size. The membrane 108 can be made of any of a variety of biocompatible materials, including, but not limited to polyurethane, PET, PETE, PETN, PTFE, polypropylene, polyacrylamide, silicone, polymethylmethacrolate, Gore-Tex®, or ePTFE with a high internodal distance. The wall thickness of the membrane 108 can be about 0.0001-0.005 inches, or about 0.0005-0.0015 inches in some embodiments. The wall thickness may vary depending on the particular material selected. In some embodiments, the pores or other perfusion openings may be laser-drilled out of the membrane material, or a heated rod or other device could be used. The membrane 108 could be either elastic or non-elastic. The membrane 108 may have either uniform or nonuniform pore sizes and areal distributions and patterns. In some embodiments, the membrane 108 can be optionally filled or coated with a radiopaque material, and may be woven, extruded or otherwise film-formed, or airlaid.

In some embodiments, one, two, or more therapeutic agents are operably attached to the membrane 108. The therapeutic agent could include an anticoagulant or clot-dissolving agent, such as, for example, heparin, hirudin, enoxaparin, fondaparinux, abciximab, epitibatide, tirofiban, aspirin, clopidogrel, warfarin, ticlopidine, tissue plasminogen activator, or urokinase. The therapeutic agent could also include an immunosuppressant or antiproliferative agent, such as, e.g., paclitaxel, rapamycin, zotarolimus, prednisone, cyclosporine, methotrexate, mycophenolate, azathioprine, 6 MP, or tacrolimus. Other drugs or bioactive compounds could also be included depending on the desired clinical result.

In some embodiments, the attachment of the membrane 108 to the frame 106 is accomplished by overlapping the membrane 108 about the wire frame 106 and heat bonding it to a backing membrane, and then trimming the bonded edge, as described hereafter. Other options for attachment include using a polymer, such as a polyurethane dispersion to coat the frame 106 and then utilizing heat bonding, adhesive bonding, suturing, self-wrapping and bonding, mechanical bonding such as an interference fit by a double frame trapping the membrane material around the edges, stitching and/or ultrasonic welding. In some embodiments, a dip process could be used to attach the membrane to the frame, similar to that of dipping a wand head into soap for blowing bubbles.

One attachment method of the membrane 108 to the frame 106 is as follows. First, the frame 106 is cleaned, such as with isopropanol, and dried completely, while the shaft 300 is similarly cleaned and dried. Dry nitrogen or another suitable agent can be used for the drying step. An attachment fixture may be used to facilitate rapid attachment. The fixture should provide a positioning jig for membrane materials, and a compressible base, such as compression foam, on which the membrane 108 and frame 106 may be positioned. A frame 106 that has been pre-assembled to a shaft 300 and fitted with sutures can then captured be in a yoke to hold the frame 106 flat. A backing membrane (not shown) is then placed on the attachment fixture. This backing membrane is preferably made from the same material as the porous membrane 108, and is provided with a pre-cut aperture of a size and shape slightly smaller than the interior dimension of the frame 106 itself. The jig-captured frame 106 is then positioned on the fixture with the frame 106 overlaying the backing membrane, and the porous membrane 108 is aligned atop the frame 106 in the fixture. A compression plate/heater is placed over the fixture and clamped in place, and heat is applied for a short time to seal the porous membrane 108 to the backing membrane. After sealing, the edges are trimmed smooth close to the frame. Finally, the shaft 300 is cleaned with isopropanol and dried.

In some embodiments, the shaft 300 is an elongate, flexible solid or hollow wire that can be made of Nitinol or other materials, examples of which are disclosed with respect to the frame 106 materials above. The shaft 300 can be designed to have flexibility, column strength, and resist stretching under tension. The shaft 300 may also include a handle portion at its device proximal end for control by a physician or other operator.

The length of the shaft 300 will depend upon the intended vascular access point. In some embodiments, the shaft 300, or the entire deflecting device including the shaft, is from about 100 cm to about 120 cm, such as about 110 cm in length to allow for manipulation through sheaths as long as 90 cm, or more. The shaft can have a low profile outer diameter, such as between about 0.030 inches and 0.040 inches, or about 0.035 inches in some embodiments so that the physician can flush contrast between the shaft and the sheath to confirm position of the shield.

Figure 8:
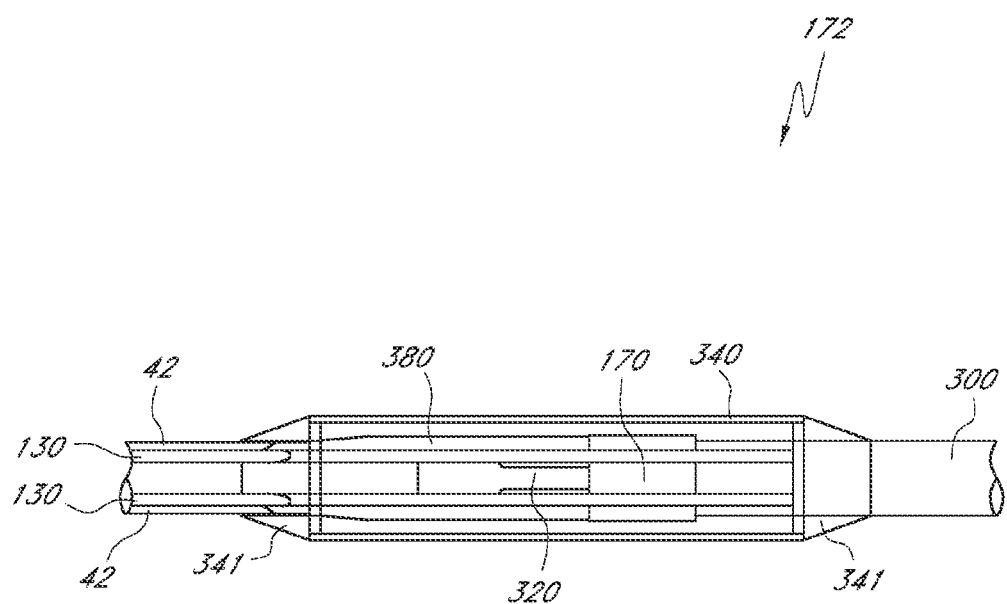
FIG. 8 illustrates one embodiment of a partial cut-away view of a shaft-frame connector for an embolic deflector.

FIG. 8 illustrates a cut-away view of one embodiment of the connection 172 of the shaft 300 to the frame 106 of the deflector 100. The shaft 300 is preferably provided with a distal (near connection to frame 106) end shape 320 that positively engages a complimentary portion of the frame attachment junction 130. The connection 172 can include complimentary male-female attachment structures, an interference fit, bonding or other adhesives, or other attachments. The connection 172 may be secured with a hypotube 340 (sleeve or collar) that may also carry a radiopaque marker 170 of the shaft 300 as described above and may provide an attachment point for the retrieval sutures 42 described elsewhere herein. Taper elements 341 which can be fillets of UV adhesive in some embodiments, provide a seal to the connection 172 and advantageously provide a smooth transition at each end of the connection 172.

One embodiment of a method of assembly of the shaft to the frame is as follows. First, the shaft 300, sutures 42, frame 106, and hypotube 340 are cleaned in isopropanol or other solvent and dried. An assembly fixture for securing the components in the proper relationship to each other and at the correct distances is preferably employed. The hypotube 340 optionally containing the radiopaque marker 170 is positioned in the fixture, and the shaft 300 is inserted fully through the hypotube 340. The shaft 300 is then interlocked to the mating feature of the frame 106 or otherwise attached, and the joint is drawn back into the hypotube 340 and locked in position with the hypotube 340 covering the joint. The sutures 42 (as described elsewhere herein are then looped around the frame 106 sides and the free ends inserted into the hypotube 340. Adhesive, such as Dymax 203-CTH-F-VLV is then wicked into the proximal end of the hypotube 340 in stages until it appears at the distal end, UV cured, and the process repeated until filling the hypotube 340. The suture 42 free ends are then trimmed flush with the proximal end of the hypotube 340. Finally, more adhesive is used to fill the proximal end of the hypotube 340 and is UV cured, creating a transition, such as a conical transition between the hypotube 340 and the shaft 300. The assembly is then heat cured in an oven at about 245° F. for approximately one hour.

Additional lumen may be provided, depending upon the desired functionality of the embolic deflection system. For example, contrast dye or other flowable media may be introduced through a second lumen on the deployment catheter, through a lumen extending through the shaft 300, or by sizing the inside diameter of the main lumen of a single lumen deployment catheter greater than the outside diameter of the guidewire or deflection device shaft to provide an elongate flow channel from the proximal manifold of the catheter to the distal opening. In addition or as an alternative to contrast dye, any of a variety of thrombolytic agents or other drugs identified elsewhere herein such as in the discussion of the membrane may be infused. Normal saline, heparinized saline, or other rinse or flush media may also be introduced, such as to clear any adherent debris from the membrane. Alternatively, a secondary lumen may be utilized to introduce any of a variety of additional structures, such as a pressure sensor to sense aortic blood pressure, or a cardiac output monitor to monitor blood flow or an emboli capture basket for positioning in the aorta downstream from the emboli deflector. Additional features may be added depending upon the desired functionality of the embolic deflection system.

Figure 8A:
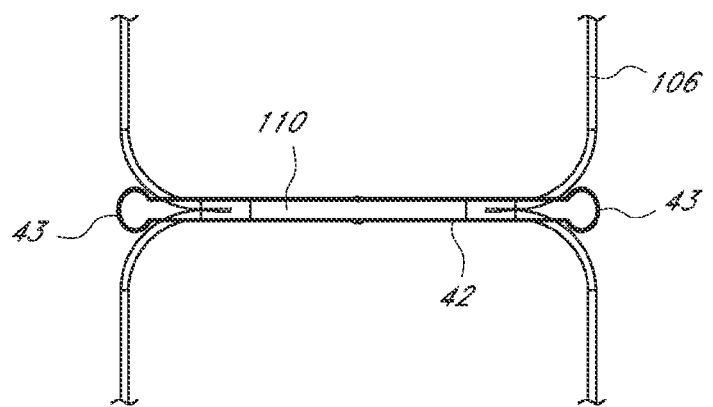
FIGS. 8A-8C illustrate various views of the deflector frame illustrating the position of the control line including looped ends, according to one embodiment of the invention.
Figure 8B:
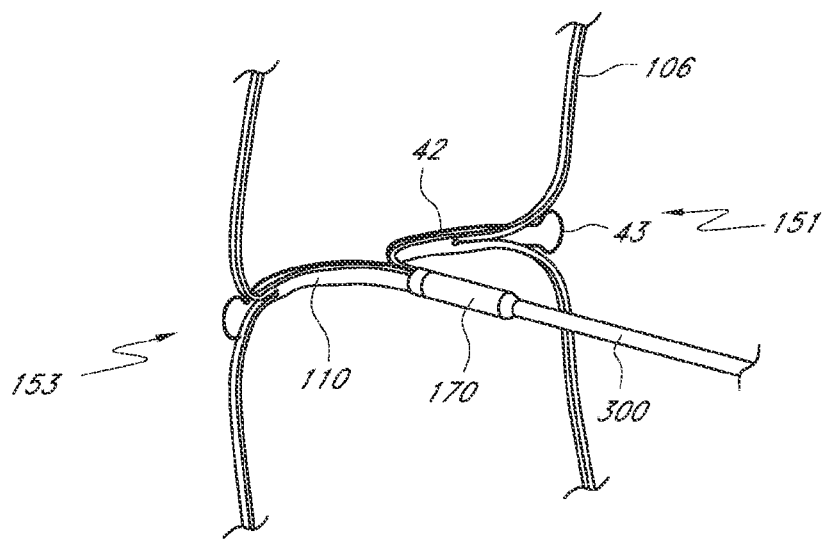
Figure 8C:
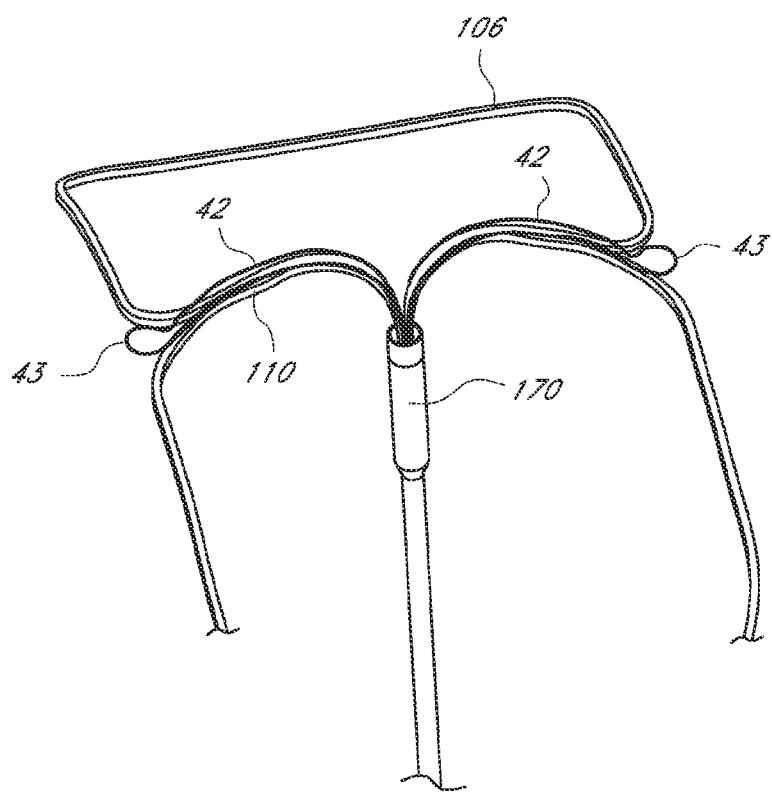
Figure 9:
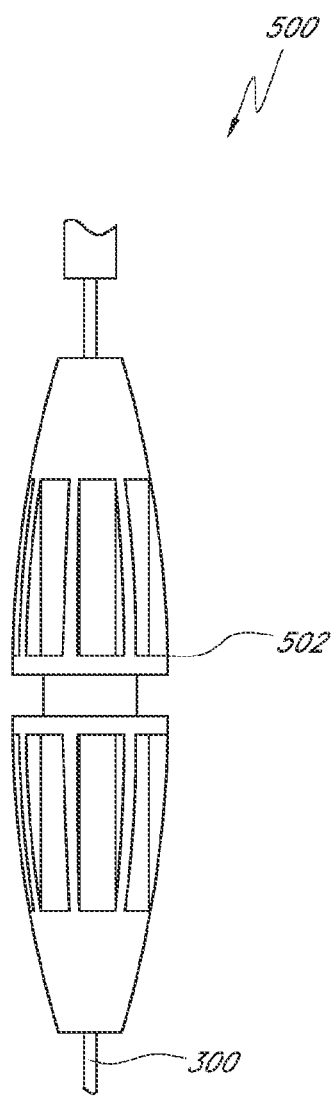
FIG. 9 illustrates one embodiment of a torque control for an embolic deflector.

As depicted in FIGS. 5 and 8 above, and in greater detail in FIGS. 8A-8C in other embodiments, one or more control lines 42 such as, for example, sutures can be used as an aid for retrieval of the deflector 100. A loop of suture 42 can be axially moveably trapped within a lumen formed by the membrane 108 heat-bond and acts to lead the membrane 108 into the sheath 102 during retrieval. Sutures may be made of any appropriate material, such as nylon, catgut, PTFE, ePTFE, polyester, polyglycolic acid, poliglecaprone, polyethylene, polypropylene, or polyurethane, depending on the desired clinical result. Alternatively, the control line 42 could be a single strand or multiple strand metal wire, or replaced by any suitable retrieval aid such as an extension of the membrane 108 itself. In other embodiments, a control line 42 or other retrieval aid is not required if the membrane attachment means does not require it for reliable retrieval.

Referring to FIGS. 8A to 8C, illustrated are various perspective views illustrating control lines 42 forming loops 43 around membrane 108 (not shown for clarity) operably connected to both transverse struts 110 and around first 151 and second 153 sides of the frame 106. As shown, proximal retraction of the control lines 42 will cause the loops 43 to lead the membrane 108 and frame 106 into the sheath 102 and assist in collapsing the deflector 100 for removal.

In one embodiment, a plurality of sutures 42 are preformed into loops that attach to the frame 106 near the shaft 300 to aid in removal and recapture of the deflector. These sutures can be suitably heat-formed into a loop of appropriate shape and size to facilitate assembly with the frame 106 and shaft 300 prior to attachment of the membrane 108 to the frame 106. The sutures 42 are preformed by wrapping the suture material around a metal jig (that could be comprised of three closely spaced metal pins arranged in a triangle) under tension and then heating the jig and suture material in an oven at about 350° F. for a sufficient time to set the suture material (typically about 30 minutes) followed by cooling and removal from the jig.

As depicted in FIG. 5, the torque control 500, which functions similar to that of a wire pin vise, is used to stabilize the deflector 100 (not shown) during packaging, and also as a proximal handle to help grip and manipulate the shaft 300 during use. Transmission of torque from the shaft 300 to the frame 106 can be particularly advantageous while manipulating the deflector 100 within the vasculature, in order to rotate a radially asymmetric deflector 100 into its desired location, such as to cover the ostia of the brachiocephalic artery and the left common carotid artery, for example. In some embodiments, the torque control 500 can be used to grip guidewires up to 0.038" in diameter and employs a clamp 502 that can be rotated in an appropriate direction by an operator to reversibly lock and unlock onto the shaft 300.

The torque transmission capability of the shaft 300 will generally decline as the shaft is made longer. Torque transmission capabilities of the shaft may be enhanced by constructing the shaft of non-polymeric material (e.g. solid metal wire or hypotube). Alternatively, shaft 300 may be fabricated such as by wrapping a first polymeric filament helically around a mandrel in a first direction, and bonding a second polymeric filament wrapped helically in a second, opposing direction around the first wrapping. Additional layers of helical wrapping or braided constructions can provide relatively high torque transmission, as is understood, for example, in the intracranial microcatheter arts.

Figure 10:
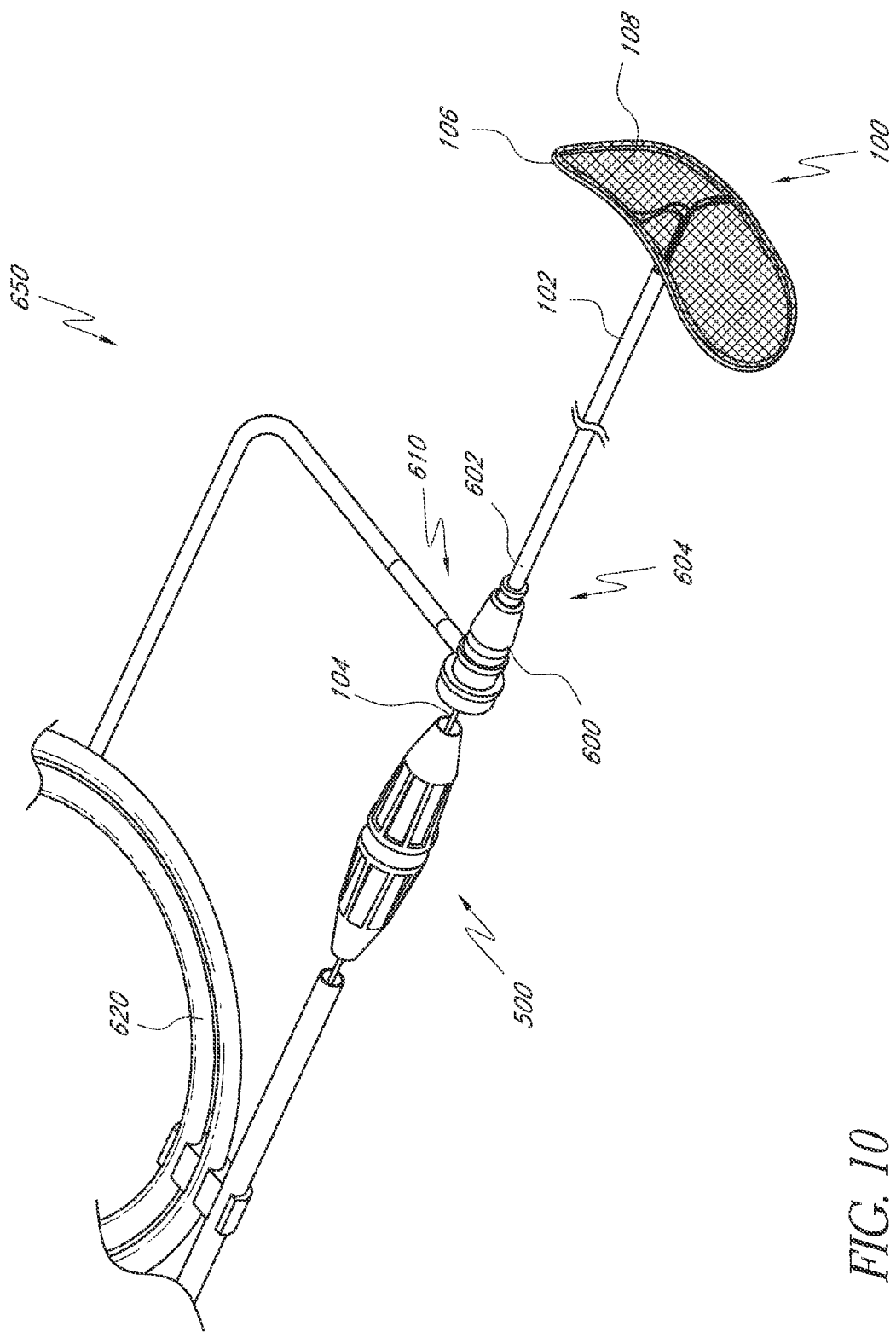
FIG. 10 illustrates components of one embodiment of an embolic deflector deployment kit.

As illustrated in FIG. 10, the device can be loaded through a loading tool, which can be operably connected to, in some embodiments, a blunt-tipped introducer sheath 604, that could be 6 French in size, that can allow the deflecting device to be flushed and back-loaded. The introducer 604 includes a silicone hemostasis valve (near 600) with introducer shaft 602 connected to a flush port 610 (with stopcock) and length of tubing 620, which can be optionally attached. The deflector 100 is initially collapsed into the loading tool to evacuate all air. The deflector 100 then passes the hemostasis valve at the proximal end 600 of the introducer sheath 604 and/or the delivery sheath 102.

In addition to the introducer 604 described above, FIG. 10 illustrates one, two, or more other components of a deflector system or kit including a deployment system 650 that can be packaged together in a sterile fashion, and ready for physician use. The system also include the deflector 100 as disclosed elsewhere herein, sheath 102 housing the shaft 300 (not shown) of the deflector 100, torque control 500 housing a length of guidewire 104, and other loading tools (not shown) as required.

Figure 11:
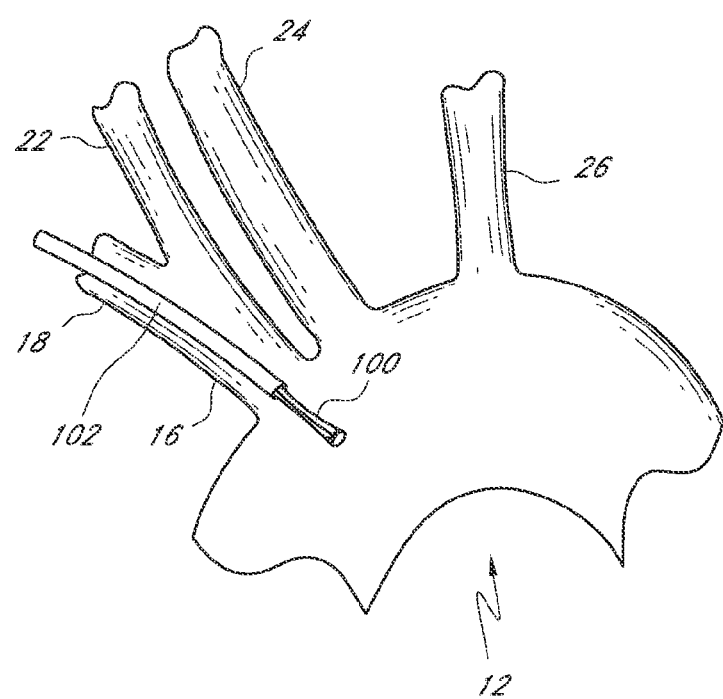
FIGS. 11-13 depict a deployment sequence for a multi-lobed embolic deflector, according to some embodiments of the invention.
Figure 12:
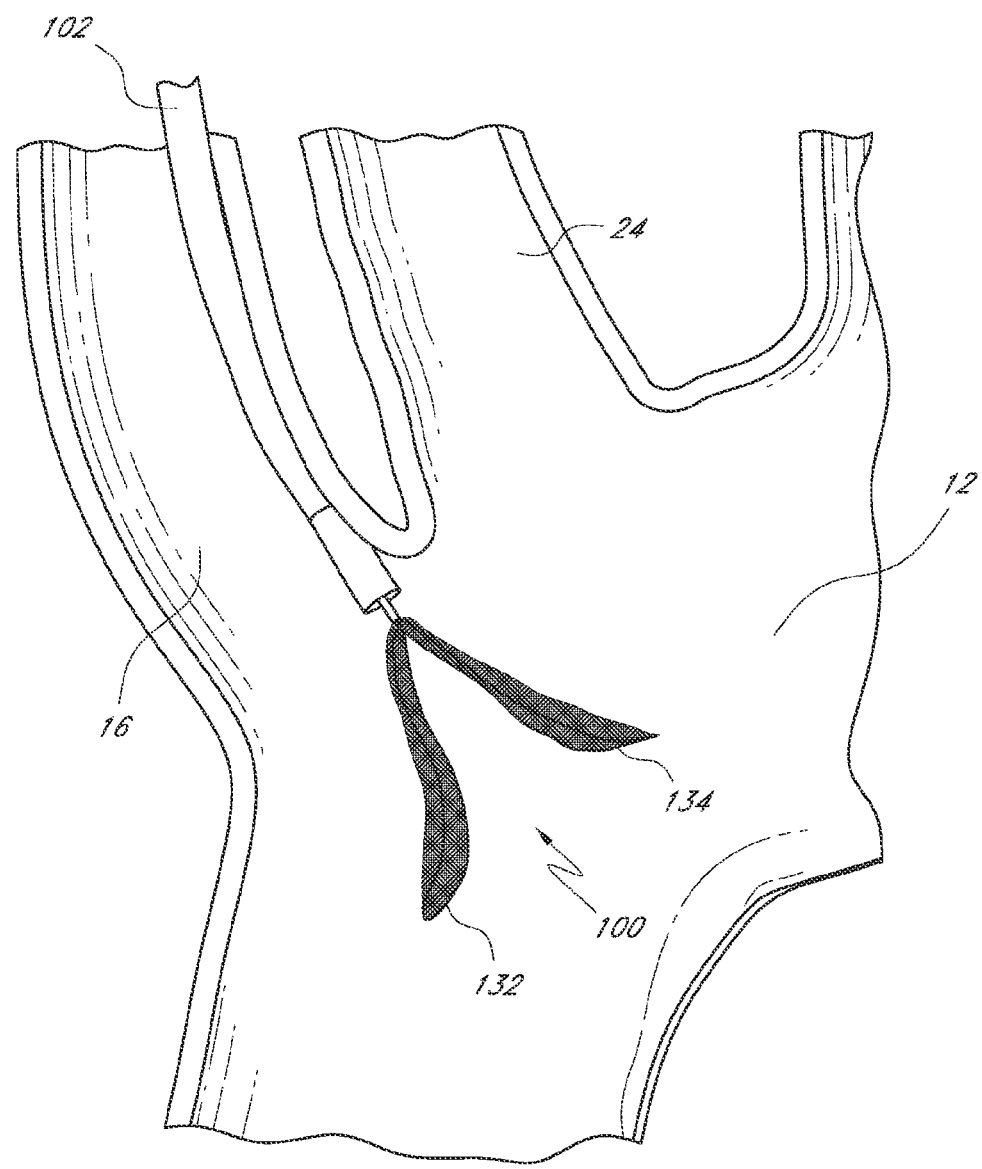
Figure 12A:
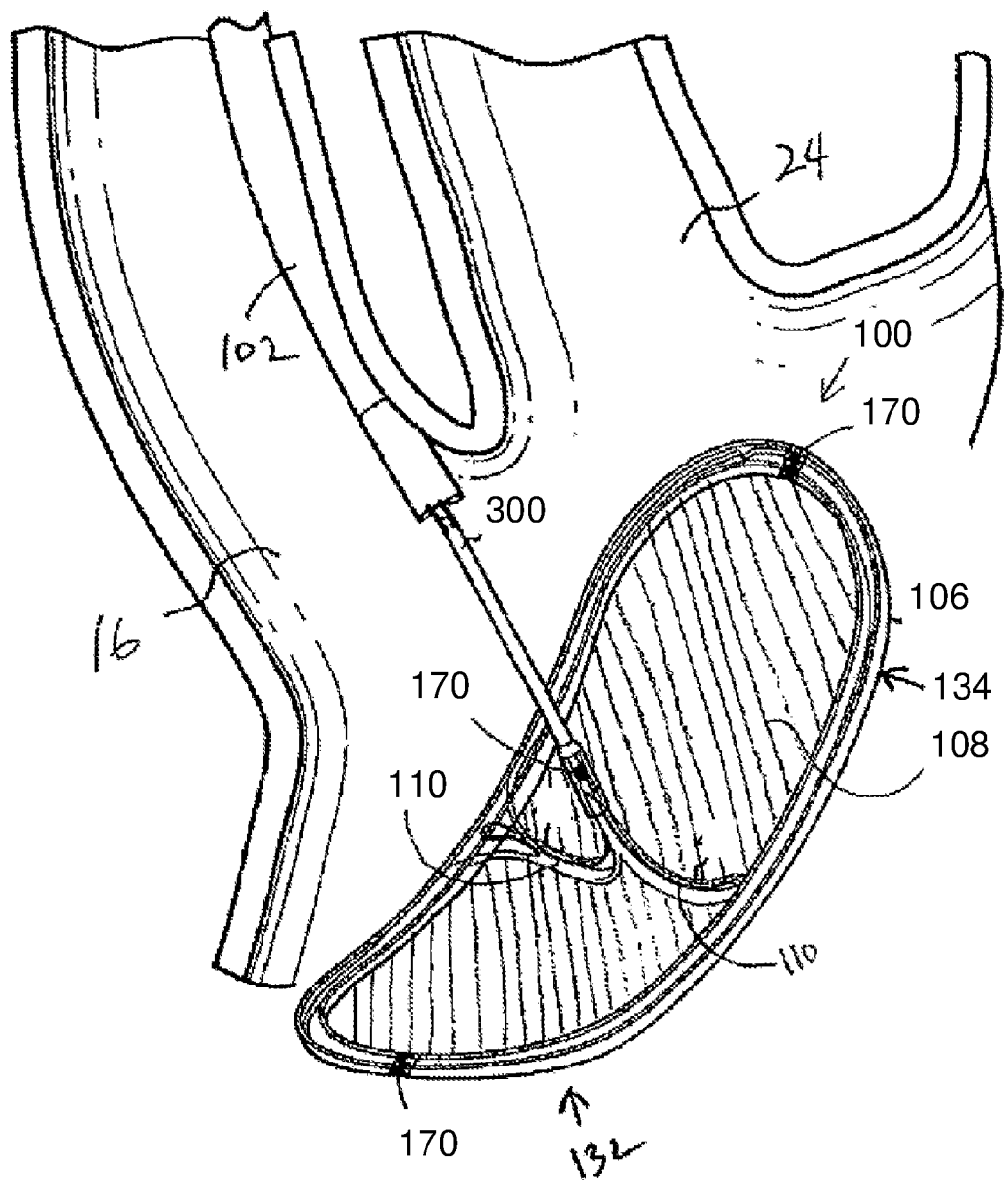
Figure 13:
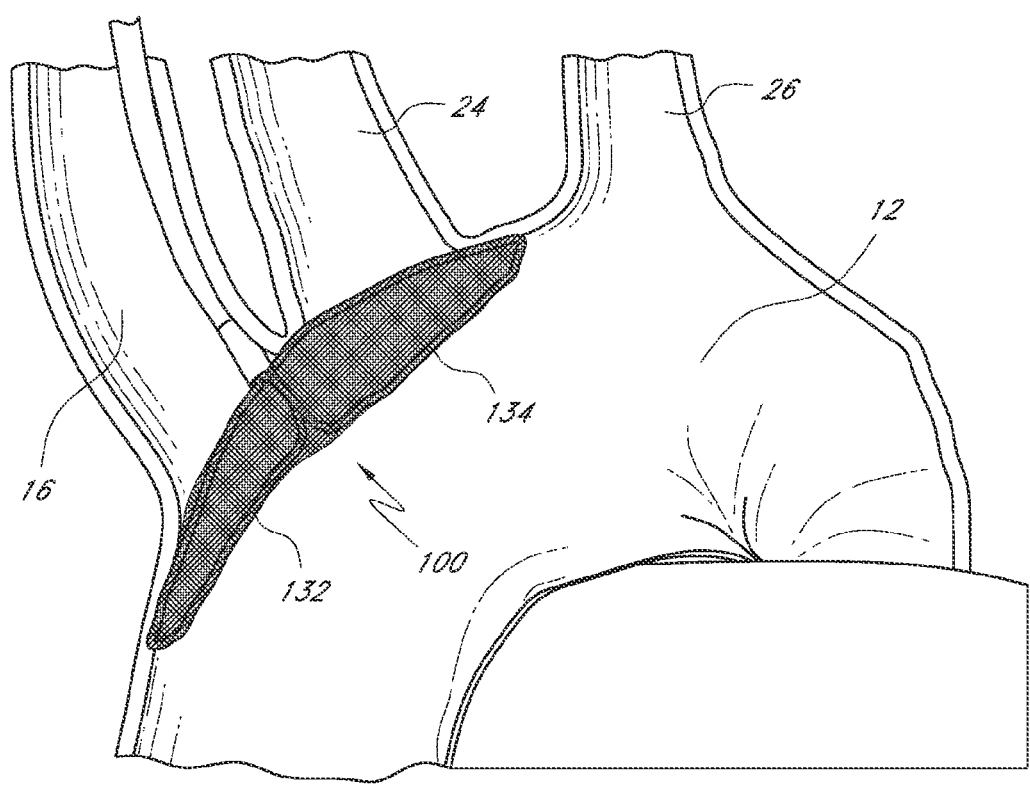
Figure 13A:
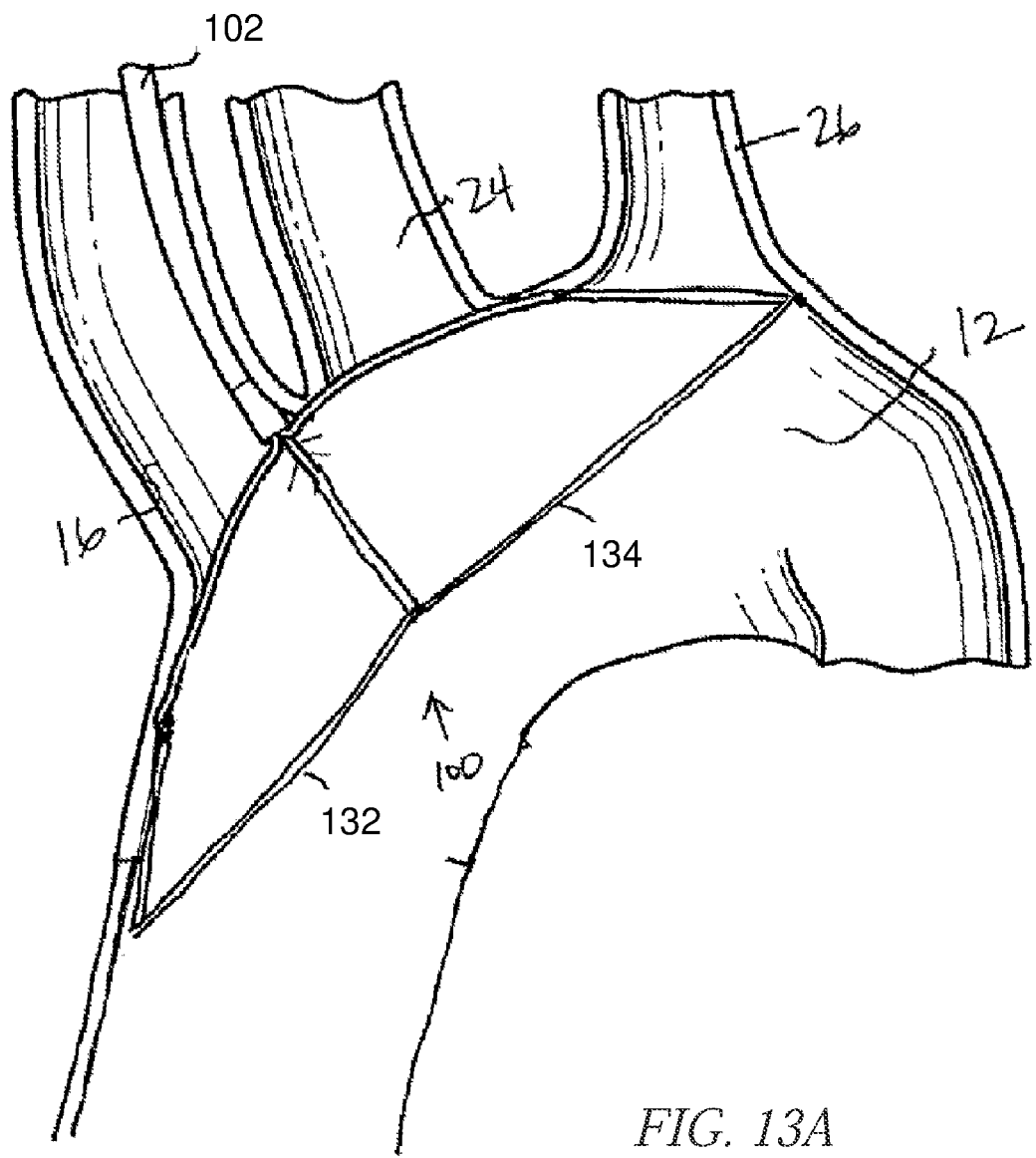
FIG. 13A depicts an embolic deflector sized and configured to cover the ostia of three side branch vessels, including the brachiocephalic, left common carotid, and left subclavian arteries.

The multi-lobed deflector 100 as illustrated in FIG. 5 can be placed and removed as described above, such as in connection with FIGS. 3A-3E (upper extremity approach), FIGS. 4A-4F (femoral approach), direct aortic puncture, or other approach as described above. An abbreviated deployment sequence for the multi-lobed deflector will be illustrated and described in connection with FIGS. 11-13. As illustrated in FIG. 11, the deflector 100 can be positioned into the aortic arch by the Seldinger or other technique via the right radial, ulnar, brachial, axillary, or subclavian artery. As shown in FIG. 12, it is advanced to the ostium of the brachiocephalic artery 16 where it is deployed in the aortic arch 12, in which the lobes 132, 134 of the deflector 100 are allowed to outwardly expand as shown in FIG. 8. The lateral ends of the deflector 100 have atraumatic tips to prevent vessel damage in some embodiments. The two opposing radiopaque markers 170 on the lateral ends of the deflector frame (illustrated, e.g., in FIG. 6B) can be visualized as one marker positioned toward the ascending aorta and the other positioned toward the descending aorta. As illustrated in FIG. 12A, the frame 106 is formed so that it is first biased into a proximally concave shape when in an unconstrained expansion. However, after traction is applied, following expansion of the deflector 100, traction can be applied by the physician and the device is then pulled back into position to cover the ostia of both the brachiocephalic 16 and left common carotid 24 arteries and traction is applied to maintain the deflector 100 in position, as shown in FIG. 13. After application of traction to form a fitting seal against the aortic wall when it is deployed, the deflector 100 can in some embodiments invert from a configuration that is concave in the direction of the ostia of the left common carotid artery as shown in FIG. 12A to a convex proximal configuration (in other words, concave towards a central axis of the aorta) as illustrated in FIG. 13. The shaft radiopaque marker and the sheath tip radiopaque marker can then be superimposed and visualized as one line. A slow flush of contrast may be used to confirm the seal over these two vessels. FIG. 13A illustrates an alternative embodiment where the deflector 100 is sized and configured to cover the ostia of three side branch vessels, including the brachiocephalic 16, left common carotid 24, and left subclavian 26 arteries. While the embodiment illustrated in FIG. 13A illustrate generally axially symmetric lobes 132, 134 depending on the desired clinical result or patient anatomy the lobes may be alternatively axially asymmetric. For example, the maximum axial length of a first lobe (e.g., 134) could be greater than, such as 10%, 20%, 30%, 40%, 50%, 75%, or more greater than the maximum axial length of a second lobe (e.g., 132). The deflector 100 can remain in place throughout the emboli causing index procedure or other elapsed period of time and then can be removed as described above.

In some embodiments, the deflector 100 can be retrieved into the sheath 102 by simply retracting the shaft 300 relative to the sheath 102. The central struts fold together in the first action, then a second fold occurs as the sheath forces the lateral ends of the lobes to be closed together. Once the deflector 100 is fully captured and changes into its collapsed configuration inside of the sheath, the sheath and deflector 100 can then be removed from the body. Variations on the procedure could be employed to minimize intimal damage and/or potential for release of emboli during retrieval. The preferred procedural variation would be for the user to advance the device and sheath tip into the aorta near the lesser curve of the arch, then re-sheath the device in that location.

FIGS. 14A-14K are top schematic views of various configurations of alternative deflector frames, according to some embodiments of the invention.

Figure 14A:
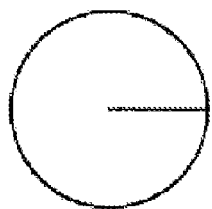
Figure 14B:
Figure 14C:
Figure 14D:
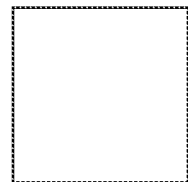
Figure 14E:
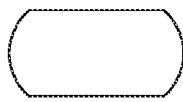
Figure 14F:

For example, in FIG. 14A, the deflector frame is radially symmetric and dome-shaped like an umbrella. The edge of the umbrella can be envisioned as a flexible, porous donut-shaped element, similar to the edge of a diaphragm, allowing a good seal with the curved aortic wall. A wire ring can define the edge in some embodiments. The dome part of the umbrella can include struts to assist in the opening and closing of the umbrella and to help maintain its position. The center of the frame can have a hub on the inside surface to which the struts are attached. The device is pushed out of the delivery catheter with a tube, wire or other member that engages this hub. This hub assists with the opening of the deflector. The hub remains attached to the deflector shaft, and the guide wire is used to pull the deflector into position. The deflector may also self-expand if made, for example, of a shape memory material, resuming its shape after being released from its sheath. The deflector may also include wires which assume their curved dome shape as they are released from the catheter. The porous membrane between the wires is attached, in some embodiments, at the highest point of the profile to assist with an umbrella-like deflection of clot or debris. The catheter itself may divide at its distal end to comprise the struts of the deflector. A single wire may be shaped into petal-like struts for the deflector which assume their umbrella shape upon exit from the delivery catheter. The device may be provided with radiopaque markers or metal parts which are radiopaque as described elsewhere in the application.

Figure 14G:
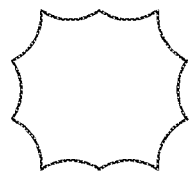
Figure 14H:
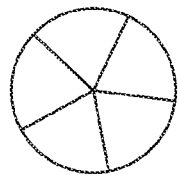
Figure 14I:
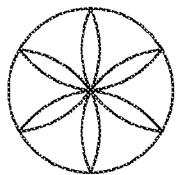
Figure 14J:
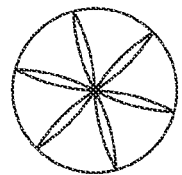
Figure 14K:
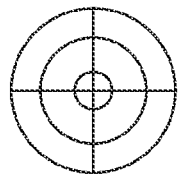

Further embodiments of top views of deflector frames illustrated include oval (FIG. 14B), rectangular (FIG. 14C), square (FIG. 14D), rectangular with rounded lateral ends (FIG. 14E), cloud-shaped (FIG. 14F), starburst-shaped (FIG. 14G). FIGS. 14H-14K illustrate phantom plan views illustrating frames with 5 struts and a central hub (FIG. 14H), having wide (FIG. 14I) and narrow (FIG. 14J) petals, or with concentric elements (FIG. 14K).

Other embodiments of the deflector frame have a rolled edge, or a flat porous edge. Another embodiment of the frame has no struts, but includes a nitinol or other biocompatible skeleton. Some embodiments include one, two, or more wires to position and anchor the device. Another embodiment of the device has anchors such as barbs, along the frame, e.g., at the lateral edges which help to maintain its position during the procedure.

Another embodiment of the deflector is parachute-like, with a ring gasket at its edge. The gasket would be held firmly in position over the ostia of the appropriate vessels, such as the brachiocephalic and left common carotid arteries. The billowy porous middle section would deflect or trap embolic debris on its exterior surface while causing minimal resistance in the aorta. The middle portion would be inverted as it is removed by pulling on wires attached to its center, capturing any clot stuck to it. Alternatively, the center of the device could be a screen, which fits more snugly against the aortic wall, with a very small profile, further preventing resistance. Again the device would be removed by inversion, capturing any emboli or thrombus that may accumulate on the membrane or other component of the deflector prior to removal.

Another embodiment of the deflecting device includes a rib-supported or self-supporting spherical frame covered by porous membrane, which may be distorted into a flat or semi-flat shape for covering one, two, or more vessel ostia by withdrawing a wire attached to one side of the sphere. The device may be oval, rectangular or of another shape, some of which are illustrated above, to assist in sealing of the edge against the wall of the aorta, covering the ostia of, for example, both the brachiocephalic and left common carotid arteries and maintaining a low profile within the lumen of the aorta. The deflector of the present invention may take alternative shapes such as: round, oval, square, rectangular, elliptical, and edge-scalloped or irregular. This device could be modified in size in another embodiment in order to be used to cover the ostia of different vessels. The device may be coated with a therapeutic agent as described elsewhere herein.

Side view depth profiles of deflector frames are illustrated in FIGS. 15A-15K. These depth profiles include onion-shaped (FIG. 15A), frustoconical (FIG. 15B), bi-level with multiple curvatures (FIG. 15C), bi-level concave-convex (FIG. 15D), flat (FIG. 15E), slightly rounded (FIG. 15F), oval (FIG. 15G), pyramidal (FIG. 15H), tent-shaped and pointed (FIG. 15I) or more rounded (FIG. 15J), tear-drop shaped (FIG. 15K), or conical with a projection that may extend to the opposite wall of the aortic lumen, such as for improved anchoring (FIG. 15L). The deflector could include 1, 2, 3, or more frame and/or membrane layers and may be comprised of overlapping or connecting components.

Figure 16A:
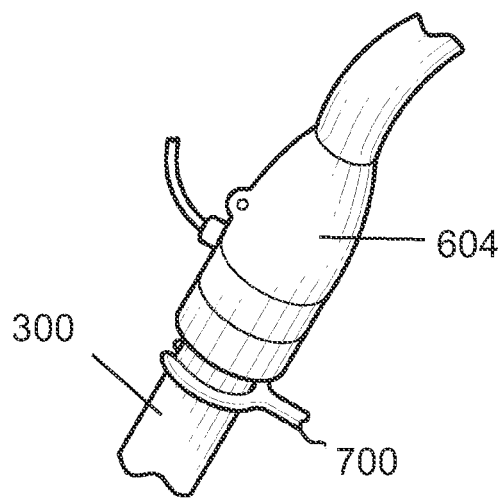
FIGS. 16A-D depict various embodiments of a locking mechanism between an embolic deflector shaft and an introducer sheath.
Figure 16B:
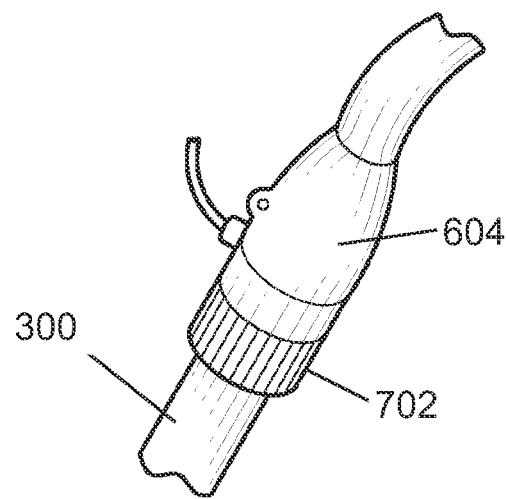
Figure 16C:
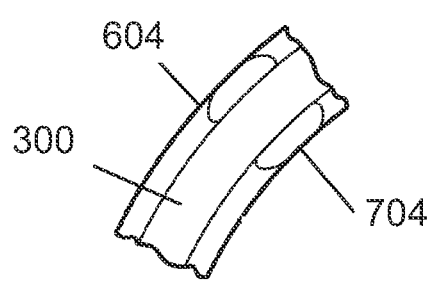
Figure 16D:
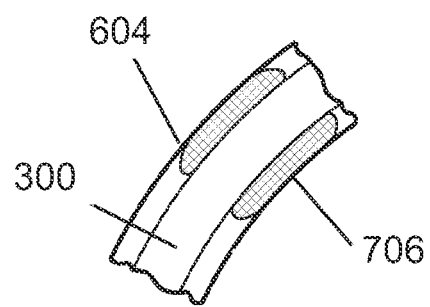

FIGS. 16A-16D illustrate different embodiments of external locking mechanisms that can assist in maintaining the deflector in a desired position in the body. FIG. 16A illustrates a clamp 700 that can fix the shaft 300 of the deflector 100 relative to the introducer sheath 604 of the deflector. FIG. 16B illustrates a threaded twist screw 702 functioning similarly to that of the clamp 700 of FIG. 16A. FIGS. 16C-D illustrates an expandable member configured to reside within the introducer sheath 604 and at least partially surround the shaft 300 of the deflector 100 to prevent proximal or distal movement of the shaft 300 within the introducer sheath 604. An inflatable balloon 704 is illustrated in FIG. 16C, that can be inflated or deflated, for example, via a separate inflation media lumen within the introducer sheath 604. A stent-like sleeve 706 is illustrated in FIG. 16D. In some embodiments, the sleeve 706 could have shape memory properties and radially expand or contract with the application of heat or cold to the sleeve 706. In some embodiments, the locking mechanism can be incorporated with the torque control as previously described.

Figures 17A, 17B:
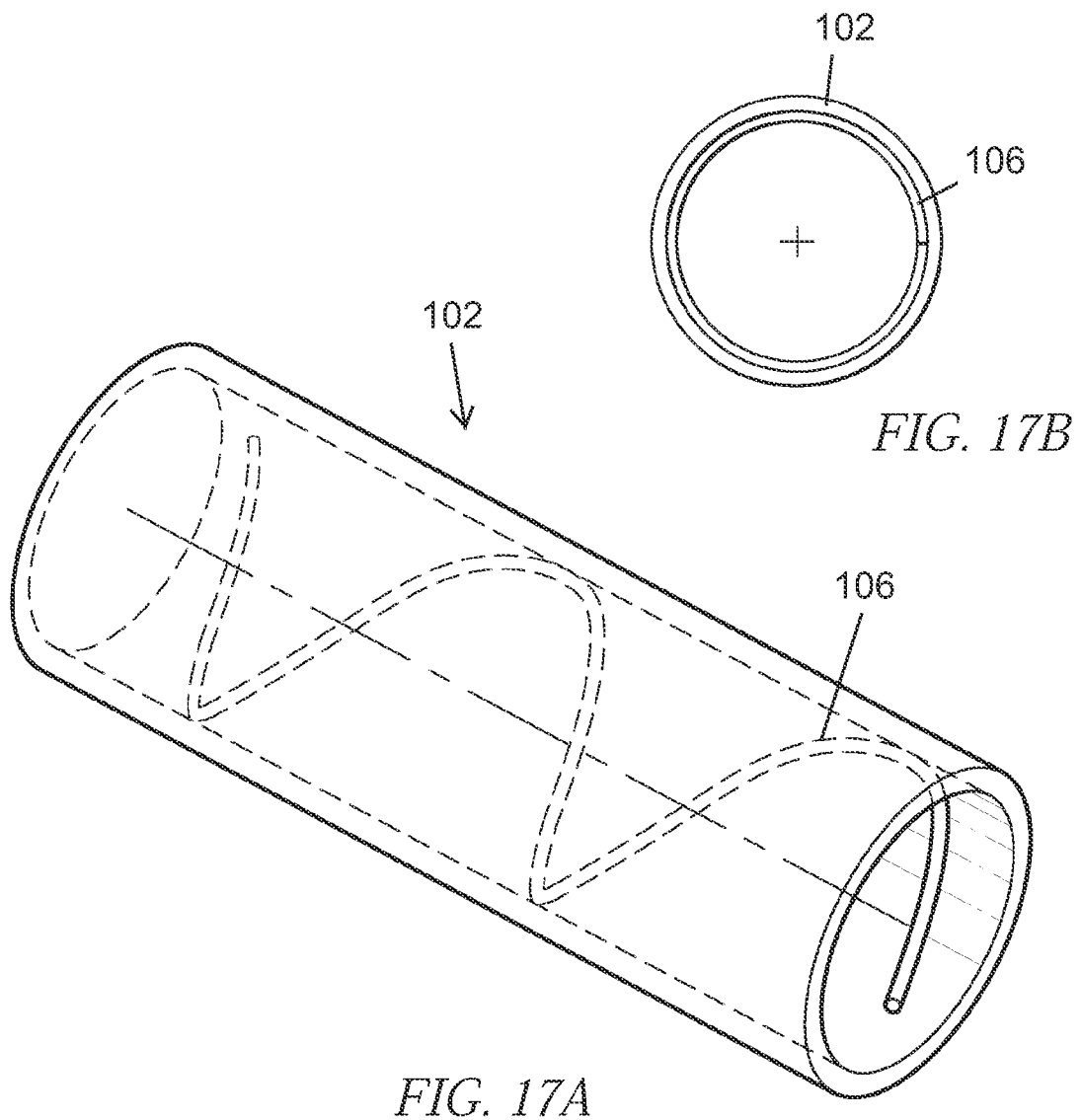
FIGS. 17A-D depict various views of another embodiment of an embolic deflector comprising a coil support which expands and flattens upon emergence from the lumen of a tubular containing structure.
Figure 17C:
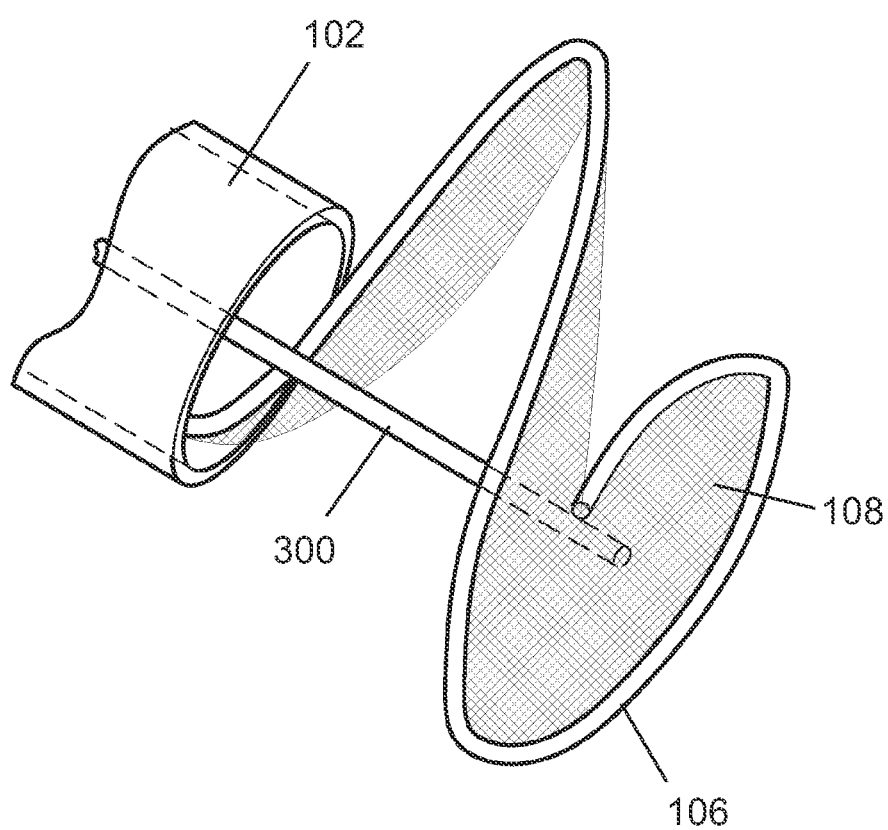
Figure 17D:
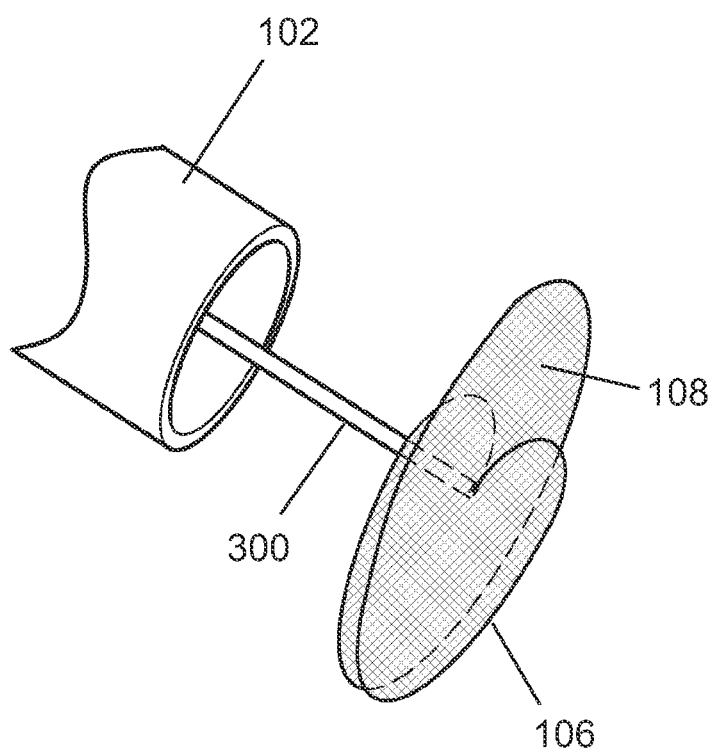

FIGS. 17A-17D illustrate another embodiment of a deflector 100, where the frame 106 is an expandable wire structure having a first end 710 and a second end 712 that expands and flattens in an unstressed configuration once removed from a delivery sheath 102. FIG. 17A illustrates in a perspective view the deflector frame 106 within the sheath 102, while a sectional view is illustrated in FIG. 17B. Partial expansion of the frame 106 is illustrated in FIG. 17C, and complete expansion is illustrated in FIG. 17D. Frame 106 is connected to membrane 108 as described further above. In some embodiments, the straight-line distance between the first end 710 and the second end 712 of the frame 106 in its expanded configuration is at least about 20%, 30%, 40%, 50%, 60%, 70%, 80%, or more shorter than the distance between the first end 710 and the second end 712 of the frame in its collapsed configuration.

Figure 18A:
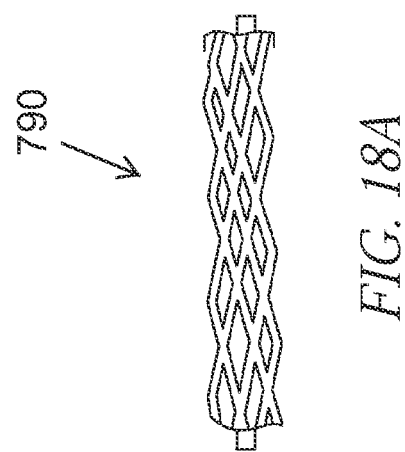
FIGS. 18A-C depict other embodiments of an embolic deflector comprising a helical (18A), spherical (18B), or onion-shaped (18C) mesh that flattens into a disc shape upon emergence from the lumen of a tubular containing structure.
Figure 18B:
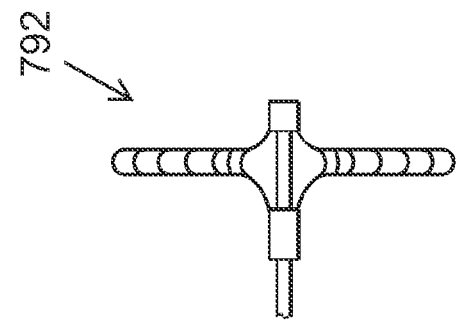
Figure 18C:
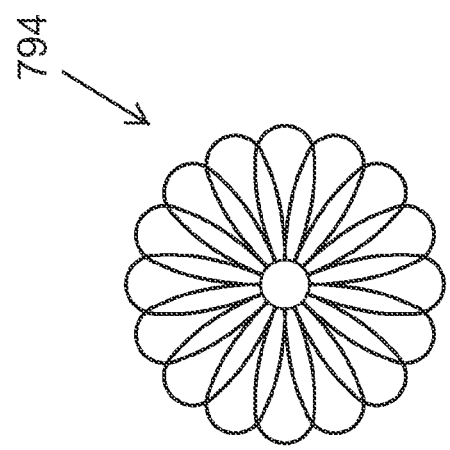

FIG. 18A-18C illustrate additional embodiments of frame 106 portions of a deflector 100 that transform from a first collapsed configuration to a second expanded configuration, wherein in which the second expanded configuration, the frame flattens into a disc, oval, or other shape as described elsewhere in the application. Collapsed configurations of a helical mesh frame 790 is illustrated in FIG. 18A; a spherical mesh frame 792 in FIG. 18B, and an onion-shaped mesh frame 794 in FIG. 18C.

Although preferred embodiments of the disclosure have been described in detail, certain variations and modifications will be apparent to those skilled in the art, including embodiments that do not provide all the features and benefits described herein. It will be understood by those skilled in the art that the present disclosure extends beyond the specifically disclosed embodiments to other alternative or additional embodiments and/or uses and obvious modifications and equivalents thereof. In addition, while a number of variations have been shown and described in varying detail, other modifications, which are within the scope of the present disclosure, will be readily apparent to those of skill in the art based upon this disclosure. It is also contemplated that various combinations or subcombinations of the specific features and aspects of the embodiments may be made and still fall within the scope of the present disclosure. Accordingly, it should be understood that various features and aspects of the disclosed embodiments can be combined with or substituted for one another in order to form varying modes of the present disclosure. Thus, it is intended that the scope of the present disclosure herein disclosed should not be limited by the particular disclosed embodiments described above.

What is claimed is:

1. A device adapted to be installed in an aortic arch of a human and reduce the risk of emboli entering the cerebral circulation as a consequence of an index procedure in the heart or the aorta, comprising:
 a wire sized to extend from outside the body through a first side branch vessel and into the aortic arch;
 an elongated introducer sheath sized to extend from outside the body over the wire and along the first side branch vessel until a distal end of the sheath is positioned in the aortic arch;
 an expandable emboli deflection device attached to a distal end of an elongate shaft and housed within the elongated introducer sheath, the emboli deflection device when expanded having a periphery in plan view defined by a nickel-titanium alloy skeleton, the periphery having a concave depth profile with a concave side facing toward the shaft, the emboli deflection device having a porous material stretched over the skeleton, the material having pores to allow the flow of blood but deflect or trap emboli, and wherein the skeleton is sized large enough to cover the ostia of each of the first side branch vessel and a second side branch vessel, the emboli deflection device further including drawstrings attached to the skeleton that enable inversion of the emboli deflection device.

2. The device of claim 1, wherein the skeleton comprises first and second longitudinally extending lobes extending in opposite directions along a long axis of the periphery.

3. The device of claim 2, wherein the emboli deflection device comprises first and second diverging struts extending from a common junction connected to the distal end of the elongate shaft.

4. The device of claim 3, wherein each of the first and second longitudinally extending lobes has opposite medial ends which are each connected to one of the first and second diverging struts.

5. The device of claim 4, wherein each of the first and second diverging struts extend distally from the common junction and diverge from the other strut to define a midplane of the emboli deflection device with the first and second longitudinally extending lobes being symmetric.

6. The device of claim 5, wherein each of the first and second longitudinally extending lobes each formed of a thin curved nickel-titanium alloy member, and the first and second diverging struts further laterally diverge in opposite lateral directions and are contiguous with the thin curved nitinol members of the first and second longitudinally extending lobes.

7. The device of claim 5, wherein the first and second longitudinally extending lobes define an oval periphery having a minor axis on the midplane and a major axis perpendicular thereto.

8. The device of claim 2, further including discrete radiopaque markers positioned at rounded ends of the first and second longitudinally extending lobes.

9. The device of claim 8, wherein the elongated periphery has a minor axis on the midplane and a major axis perpendicular thereto, and the discrete radiopaque markers are positioned offset from the major axis to avoid interfering with retracting the emboli deflection device into the elongated introducer sheath.

* * * * *